(12) United States Patent
Gao et al.

(10) Patent No.: US 8,217,052 B2
(45) Date of Patent: Jul. 10, 2012

(54) SUBSTITUTED TETRAHYDROPYRAN SPIRO PYRROLIDINONE AND PIPERIDINONE, PREPARATION AND THERAPEUTIC USE THEREOF

(75) Inventors: Zhongli Gao, Bridgewater, NJ (US); Ryan Hartung, Bridgewater, NJ (US); David Stefany, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/151,925

(22) Filed: Jun. 2, 2011

(65) Prior Publication Data

US 2011/0251225 A1 Oct. 13, 2011

Related U.S. Application Data

(63) Continuation of application No. PCT/US2009/066666, filed on Dec. 4, 2009.

(60) Provisional application No. 61/120,087, filed on Dec. 5, 2008.

(30) Foreign Application Priority Data

Aug. 28, 2009 (FR) ...................................... 09 55909

(51) Int. Cl.
*A61K 31/438* (2006.01)
*A61K 31/454* (2006.01)
*A61K 31/4545* (2006.01)
*A61K 31/407* (2006.01)
*C07D 491/107* (2006.01)
*C07D 401/04* (2006.01)
*C07D 401/14* (2006.01)
*C07D 401/02* (2006.01)

(52) U.S. Cl. ........ 514/278; 514/318; 514/326; 514/409; 548/410; 546/13; 546/208

(58) Field of Classification Search .................... None
See application file for complete search history.

(56) References Cited

U.S. PATENT DOCUMENTS

| | | | |
|---|---|---|---|
| 3,258,276 | A | 6/1966 | Grogan et al. |
| 7,223,788 | B2 | 5/2007 | Schwink et al. |
| 2007/0142358 | A1 | 6/2007 | Nettekoven et al. |
| 2009/0137562 | A1 | 5/2009 | Allison et al. |
| 2010/0173898 | A1 | 7/2010 | Czechtizky et al. |
| 2010/0173949 | A1 | 7/2010 | Czechtizky et al. |

FOREIGN PATENT DOCUMENTS

| | | |
|---|---|---|
| EP | 1669350 | 6/2006 |
| WO | WO 2004/037257 | 5/2004 |
| WO | WO 2007/133561 | 11/2007 |
| WO | WO 2009/039431 | 3/2009 |
| WO | WO 2009/052063 | 4/2009 |
| WO | WO 2009/052065 | 4/2009 |

OTHER PUBLICATIONS

U.S. Appl. No. 13/151,946, filed Jun. 2, 2011, Gao, et al.
Ivan Der Poel, A. M , et al., Temporal Patterning of Ultrasonic Distress Calls in the Adult Rat: Effects of Morphine and Benzodiazepines, Psychopharmacology, (1989,) vol. 97, pp. 147-148.
Esbenshade, T. A., et al., Histamine H3 Receptor Antagonists: Preclinical Promise for Treating Obesity and Cognitive Disorders, Molecular Interventions, (2006). vol. 6, No. 2, pp. 77-88.
Hancock, A. A., et al., The Challenge of Drug Discovery of a GPCR Target: Analysis of Preclinical Pharmacology of Histamine H3 Antagonists/Inverse Agonists, Biochemical Pharmacology, vol. 71, (2006), pp. 1103-1113.
Nagumo, S., et al., Synthesis of (−)-TAN1251A Using 4-Hydroxy-L-Proline as a Chiral Source, Tetrahedron, vol. 58, (2002), pp. 9871-9877.
Porsolt, et al., Depression: A New Animal Model Sensitive to Antidepressant Treatments, Nature, vol. 266, (1977), pp. 730-732.
Stafford, J. A., et al., Asymmetric Total Syntheis of (−)-Secodaphniphylline, J. Org. Chem., (1990), vol. 55, pp. 5433-5434.
International Search Report for WO2010/065798 dated Jun. 10, 2010.

*Primary Examiner* — Yong Chu
*Assistant Examiner* — Michael Barker
(74) *Attorney, Agent, or Firm* — Kelly L. Bender

(57) ABSTRACT

The present disclosure relates to a series of substituted N-phenyl-bipyrrolidine carboxamides of formula (I):

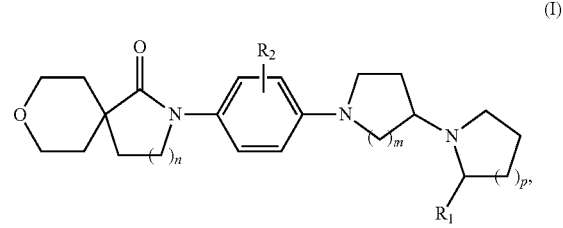

(I)

wherein $R_1$, $R_2$, m, n and p are as described herein. More specifically, the compounds of this invention are modulators of H3 receptors and are, therefore, useful as pharmaceutical agents, especially in the treatment and/or prevention of a variety of diseases modulated by H3 receptors including diseases associated with the central nervous system. Additionally, methods of preparation of substituted N-phenyl-bipyrrolidine carboxamides and intermediates therefore are disclosed.

31 Claims, No Drawings

SUBSTITUTED TETRAHYDROPYRAN SPIRO PYRROLIDINONE AND PIPERIDINONE, PREPARATION AND THERAPEUTIC USE THEREOF

This application is a continuation of International Application No. PCT/US2009/066666, filed Dec. 4, 2009, which claims the benefit of priority of U.S. Provisional Application No. 61/120,087, filed Dec. 5, 2008, both of which are incorporated herein by reference.

BACKGROUND OF THE INVENTION

1. Field of the Invention

The present invention relates to a series of substituted tetrahydropyran spiro pyrrolidinone and piperidinone derivatives. The compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also relates to methods of preparation of substituted tetrahydropyran spiro pyrrolidinone and piperidinone and intermediates therefor.

2. Description of the Art

Histamine is a ubiquitous messenger molecule released from mast cells, enterochromaffin-like cells, and neurons. The physiological actions of histamine are mediated by four pharmacologically defined receptors (H1, H2, H3 and H4). All histamine receptors exhibit seven transmembrane domains and are members of the G-protein-coupled receptor superfamily (GPCRs).

The H1 receptor was the first member of the histamine receptor family to be pharmacologically defined, with the development of classical antihistamines (antagonists), such as diphenhydramine and fexofenadine. While antagonism of the H1 receptor of the immune system is commonly used for the treatment of allergic reactions, the H1 receptor is also expressed in various peripheral tissues and the central nervous system (CNS). In the brain, H1 is involved in the control of wakefulness, mood, appetite and hormone secretion.

The H2 receptor is also expressed in the CNS, where it may modulate several processes, including cognition. However, H2 receptor antagonists have primarily been developed to ameliorate gastric ulcers by inhibiting histamine-mediated gastric acid secretion by parietal cells. Classic H2 antagonists include cimetidine, ranitidine, and famotidine.

It should further be noted that H4 receptor function remains poorly defined, but may involve immune regulation and inflammatory processes.

On the other hand, H3 receptors have also been pharmacologically identified in the CNS, heart, lung, and stomach. The H3 receptor differs significantly from other histamine receptors, exhibiting low sequence homology (H1: 30%, H2: 28%, H4: 51%). H3 is a presynaptic autoreceptor on histamine neurons in the brain and a presynaptic heteroreceptor in non-histamine-containing neurons in both the central and peripheral nervous systems. In addition to histamine, H3 also modulates the release and/or synthesis of other neurotransmitters, including acetylcholine, dopamine, norepinepherin and serotonin. Of particular note, presynaptic modulation of histamine release by H3 allows significant regulation of H1 and H2 receptors in the brain. Modulating multiple neurotransmitter signaling pathways, H3 may contribute to varied physiological processes. Indeed, extensive preclinical evidence indicates that H3 plays a role in cognition, sleep-wake cycle and energy homeostasis.

Modulators of H3 function may be useful in the treatment of central nervous system disorders, such as cognitive impairment associated with schizophrenia (CIAS), dementia of Alzheimer Type (DAT), schizophrenia, Alzheimer's disease, attention-deficit hyperactivity disorder, Parkinson's disease, depression, and epilepsy, sleep disorders (narcolepsy and insomnia), cardiovascular disorders (acute myocardial infarction), respiratory disorders (asthma), obesity, and gastrointestinal disorders. See generally, Hancock. Biochem. Pharmacol. Apr. 14, 2006; 71(8):1103-13 and Esbenshade et al. Mol Interv. April 2006; 6(2):77-88, 59.

U.S. Pat. No. 7,223,788 discloses a series of compounds, including substituted bis-pyrrolidines, having melanin concentrating hormone (MCH) receptor antagonists. But the compounds disclosed therein are not reported to be active at the H3 receptor site.

All of the references described herein are incorporated herein by reference in their entirety.

Accordingly, it is an object of this invention to provide a series of substituted tetrahydropyran spiro pyrrolidinone and piperidinone as selective H3 receptor ligands for treatment of H3 receptor regulated CNS disorders.

It is also an object of this invention to provide processes for the preparation of the substituted tetrahydropyran spiro pyrrolidinone and piperidinone as disclosed herein.

Other objects and further scope of the applicability of the present invention will become apparent from the detailed description that follows.

SUMMARY OF THE INVENTION

It has now been found that the compounds of formula (I) are useful as H3 receptor antagonists and/or inverse agonists. Thus in accordance with the practice of this invention there is provided a compound of formula (I):

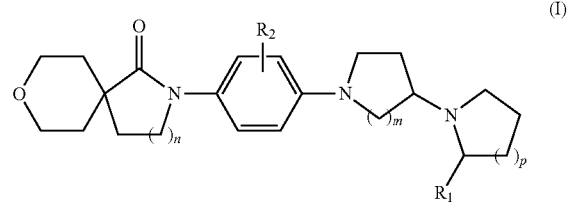

wherein
m is 1 or 2.
n is 1 or 2.
p is 1 or 2.
$R_1$ is hydrogen, $(C_1-C_4)$alkyl, $CF_3$, or $(C_1-C_4)$alkoxy-$(C_1-C_4)$alkyl.
$R_2$ is hydrogen, halogen, $(C_1-C_4)$alkyl or $CF_3$.

This invention further includes various salts of the compounds of formula (I) including various enantiomers or diastereomers of compounds of formula (I).

In other aspects of this invention there are also provided various pharmaceutical compositions comprising one or more compounds of formula (I) as well as their therapeutic use in alleviating various diseases which are mediated in-part and/or fully by H3 receptors.

DETAILED DESCRIPTION OF THE INVENTION

The terms as used herein have the following meanings:

As used herein, the expression "$(C_1-C_4)$alkyl" includes methyl and ethyl groups, and straight-chained or branched propyl, and butyl groups. Particular alkyl groups are methyl, ethyl, n-propyl, isopropyl and tert-butyl. Derived expressions such as "$(C_1-C_4)$alkoxy", "$(C_1-C_4)$alkoxy$(C_1-C_4)$alkyl", or "hydroxy$(C_1-C_4)$alkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, nitric acid, sulfamic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, propionic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound of the formula I:

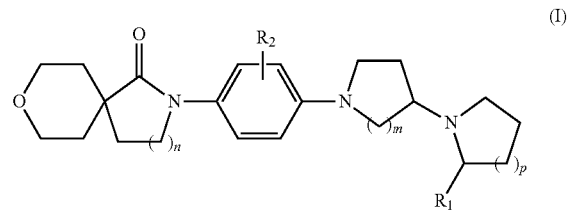

wherein
m is 1 or 2.
n is 1 or 2.
p is 1 or 2.

R₁ is hydrogen, $(C_1-C_4)$alkyl, $CF_3$, or $(C_1-C_4)$alkoxy-$(C_1-C_4)$alkyl.

R₂ is hydrogen, halogen, $(C_1-C_4)$alkyl or $CF_3$.

This invention further includes various salts of the compounds of formula (I) including various enantiomers or diastereomers of compounds of formula (I). As noted hereinabove and by way of specific examples hereafter all of the salts that can be formed including pharmaceutically acceptable salts are part of this invention. As also noted hereinabove and hereafter all of the conceivable enantiomeric and diastereomeric forms of compounds of formula (I) are part of this invention.

In one of the embodiments, there is provided the compounds of formula (I) wherein m, n and p are 1. R₁ is methyl, ethyl, isopropyl, n-propyl or methoxymethyl. R₂ is hydrogen, fluorine, chlorine, methyl, ethyl or $CF_3$.

In another embodiment of this invention there is also provided a compound of formula (I), wherein n is 2 and m is 1 or n is 1 and m is 2. p is 1 or 2. R₁ is methyl, ethyl, isopropyl, n-propyl or methoxymethyl. R₂ is hydrogen, fluorine, chlorine, methyl, ethyl or $CF_3$.

In a further aspect of this invention the following compounds encompassed by the scope of this invention without any limitation may be enumerated:

2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4,5]decan-1-one;
2-[3-fluoro-4-((2S,3'S)-2-methyl-[1,3']bipyrrolidinyl-1'-yl)-phenyl]-8-oxa-2-aza-spiro[4.5]decan-1-one;
2-{2-methyl-4-[4-((S)-2-methyl-pyrrolidin-1-yl)-piperidin-1-yl]-phenyl}-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-[4-(2-ethyl-[1,3']bipyrrolidinyl-1'-yl)-2-fluoro-phenyl]-8-oxa-2-aza-spiro[4.5]decan-1-one;
2-[2-fluoro-4-(2-isopropyl-[1,3']bipyrrolidinyl-1'-yl)-phenyl]-8-oxa-2-aza-spiro[4.5]decan-1-one;
2-[2-fluoro-4-(2-propyl-[1,3']bipyrrolidinyl-1'-yl)-phenyl]-8-oxa-2-aza-spiro[4.5]decan-1-one;
2-{2-fluoro-4-[4-((S)-2-methyl-pyrrolidin-1-yl)-piperidin-1-yl]-phenyl}-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((S)-2-methyl-[1,4']bipiperidinyl-1'-yl)-phenyl]-8-oxa-2-aza-spiro[4.5]decan-1-one;
2-{4-[4-(2-isopropyl-pyrrolidin-1-yl)-piperidin-1-yl]-phenyl}-8-oxa-2-aza-spiro[4.5]decan-1-one;
2-{4-[4-(2-propyl-pyrrolidin-1-yl)-piperidin-1-yl]-phenyl}-8-oxa-2-aza-spiro[4,5]decan-1-one;
2-[4-(2-methoxymethyl-[1,3']bipyrrolidinyl-1'-yl)-phenyl]-8-oxa-2-aza-spiro[4.5]decan-1-one;
2-{4-[4-((S)-2-methyl-pyrrolidin-1-yl)-piperidin-1-yl]-phenyl}-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;
2-{4-[4-(2-ethyl-pyrrolidin-1-yl)-piperidin-1-yl]-2-trifluoromethyl-phenyl}-8-oxa-2-aza-spiro[4.5]decan-1-one;
2-{4-[4-(2-isopropyl-pyrrolidin-1-yl)-piperidin-1-yl]-2-trifluoromethyl-phenyl}-8-oxa-2-aza-spiro[4.5]decan-1-one;
2-[4-(2-propyl-[1,3']bipyrrolidinyl-1'-yl)-2-trifluoromethyl-phenyl]-8-oxa-2-aza-spiro[4.5]decan-1-one;
2-{4-[4-((S)-2-methyl-pyrrolidin-1-yl)-piperidin-1-yl]-2-trifluoromethyl-phenyl}-8-oxa-2-aza-spiro[4.5]decan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[4-((S)-2-methyl-[1,4']bipiperidinyl-1'-yl)-2-trifluoromethyl-phenyl]-8-oxa-2-aza-spiro[4.5]decan-1-one;
2-{2-ethyl-4-[4-(2-propyl-pyrrolidin-1-yl)-pipendin-1-yl]-phenyl}-8-oxa-2-aza-spiro[4.5]decan-1-one;
2-{2-ethyl-4-[4-(2-methoxymethyl-pyrrolidin-1-yl)-pipendin-1-yl]-phenyl}-8-oxa-2-aza-spiro[4.5]decan-1-one;
2-[2-ethyl-4-((2S,3S')-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3'S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;
2-[2-methyl-4-(2-methyl-[1,3']bipyrrolidinyl-1'-yl)-phenyl]-8-oxa-2-aza-spiro[4.5]decan-1-one;
2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one.

All of the above compounds may also include corresponding salts wherever possible including the pharmaceutically acceptable salts thereof.

In another aspect of this invention the following compounds encompassed by compound of formula (I) of this invention without any limitation may be enumerated:

2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[3-fluoro-4-(2S,3'S)-2-methyl-[1,3']bipyrrolidinyl-1'-yl)-phenyl]-8-oxa-2-aza-spiro[4.5]decan-1-one;
2-{2-methyl-4-[4-((S)-2-methyl-pyrrolidin-1-yl)-piperidin-1-yl]-phenyl}-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-{2-fluoro-4-[4-((S)-2-methyl-pyrrolidin-1-yl)-piperidin-1-yl]-phenyl}-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((S)-2-methyl-[1,4']bipiperidinyl-1'-yl)-phenyl]-8-oxa-2-aza-spiro[4.5]decan-1-one;
2-{4-[4-((S)-2-methyl-pyrrolidin-1-yl)-piperidin-1-yl]-phenyl}-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;

2-{4-[4-((S)-2-methyl-pyrrolidin-1-yl)-piperidin-1-yl]-2-trifluoromethyl-phenyl}-8-oxa-2-aza-spiro[4.5]decan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[4-((S)-2-methyl-[1,4']bipiperidinyl-1'-yl)-2-trifluoromethyl-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3'S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;
2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one.

Again all of the conceivable salts of the above noted compounds including the pharmaceutically acceptable salts are part of this invention.

In a further aspect of this invention, the following compounds within the scope of this invention may be enumerated:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[3-fluoro-4-((2S,3'S)-2-methyl-[1,3']bipyrrolidinyl-1'-yl)-phenyl]-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3'S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;
2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one.

Again all of the conceivable salts of the above noted compounds including the pharmaceutically acceptable salts are part of this invention.

In a further aspect of this invention, the following compounds within the scope of this invention may be enumerated:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one.

Again all of the conceivable salts of the above noted compounds including the pharmaceutically acceptable salts are part of this invention.

In a further aspect of this invention, the following compounds within the scope of this invention may be enumerated:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one; and
2-[4-((2S,3'S)-2-methyl-[1,3']bipyrrolidinyl-1'-yl)-phenyl]-9-oxa-2-aza-spiro[5.5]undecan-1-one.

Again all of the conceivable salts of the above noted compounds including the pharmaceutically acceptable salts are part of this invention.

In another aspect of this invention the compound of this invention may be represented by a specific stereoisomeric form of formula (II):

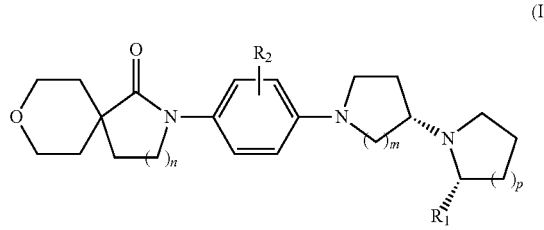

(II)

wherein $R_1$, $R_2$, m, n and p are as defined hereinabove.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. For instance, see R. C. Larock, "Comprehensive Organic Transformations," VCH publishers, 1989.

It is also well known that in various organic reactions it may be necessary to protect reactive functional groups, such as for example, amino groups, to avoid their unwanted participation in the reactions. Conventional protecting groups may be used in accordance with standard practice and known to one of skilled in the art, for example, see T. W. Greene and P. G. M. Wuts in "Protective Groups in Organic Chemistry" John Wiley and Sons, Inc., 1991. For example, suitable amine protecting groups include without any limitation sulfonyl (e.g., tosyl), acyl (e.g., benzyloxycarbonyl or t-butoxycarbonyl) and arylalkyl (e.g., benzyl), which may be removed subsequently by hydrolysis or hydrogenation as appropriate. Other suitable amine protecting groups include trifluoroacetyl [—C(═O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with TFA.

More specifically, the compounds disclosed herein and various precursors used therefor can be synthesized according to the following procedures of Schemes 1-7, wherein $R_1$, $R_2$, m, n and p are as defined for Formula I unless otherwise indicated.

For instance, Scheme 1 illustrates the preparation of the intermediate of formula (4), wherein $R_1$, m and p are as defined herein. First, in step 1, Scheme 1, suitably protected (for example tert-butyloxycarbonyl (boc)) pyrrolidinone of formula (1) is condensed with a desired substituted pyrrolidine of formula (2) by any of the known reductive amination procedures to form an intermediate of formula (3). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (3).

In step 2, Scheme 1, the intermediate (3) is then de-protected to form the desired [1, 3']-pyrrolidinyl-pyrrolidine of formula (4). Such deprotection reactions are generally carried out under acidic conditions, for example, in the presence of hydrochloric acid at sub-ambient to ambient temperatures, for example in the temperature range of about −10° C. to room temperature. However, other suitable reaction temperatures can also be used depending upon the nature of the intermediate of formula (3).

Scheme 1

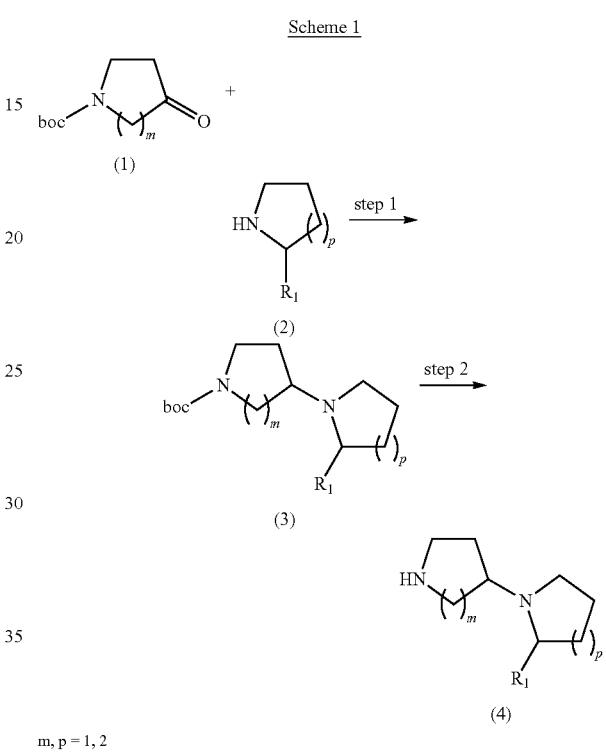

m, p = 1, 2

Scheme 2 illustrates preparation of enantiomerically pure isomers of the [1,3'] pyrrolidinyl-pyrrolidine of formula (9), wherein $R_1$, m and p are as defined herein. In step 1, Scheme 2, suitably protected (for example boc) pyrrolidine or piperidine alcohol of formula (5) is treated with p-toluene sulfonyl chloride to form intermediate of formula (6). This reaction can be carried out using any of the procedures known to one skilled in the art, such as for example carrying out the reaction in the presence of a suitable base such as triethylamine and DMAP in a suitable organic solvent, preferably an aprotic solvent such as dichloromethane at sub-ambient or ambient temperature conditions.

In step 2, Scheme 2, the intermediate of formula (6) is condensed with a desired pyrrolidine or piperidine of formula (7). Again, such condensation reactions can be carried out using any of the procedures known to one skilled in the art in order to obtain the intermediate of formula (8). Typically, such condensation reactions are carried out in the presence of a base such as potassium carbonate in the presence of solvents such as acetonitrile at ambient to super-ambient temperature conditions.

In step 3, Scheme 2, the intermediate of formula (8) is then reacted with an acid, such as hydrochloric acid in a suitable solvent, such as dioxane, to form the desired stereospecific isomer of intermediate of formula (9). It has now been found that the intermediates of formula (9) can be readily formed in accordance with the process of this invention with high enantiomeric purity, specific details of which are provided hereinbelow by way of various examples. In general, the enantiomeric purity can be determined by chiral HPLC.

Scheme 2

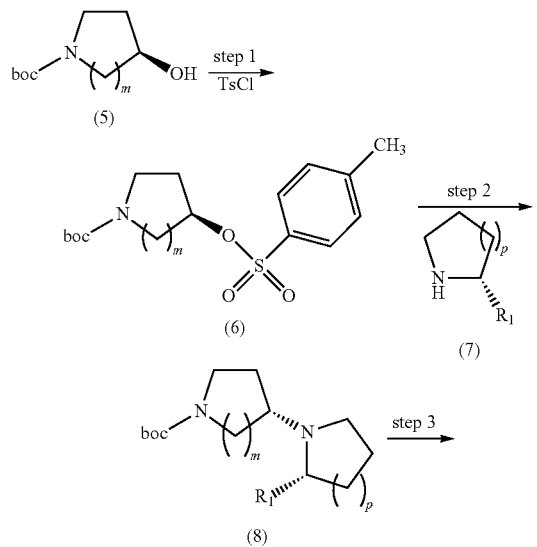

m = 1 or 2; p = 1 or 2

Scheme 3 illustrates the preparation of amino-phenyl-pyrrolidinyl-pyrrolidine intermediate of formula (12), wherein $R_1$, $R_2$, m and p are as defined herein. In step 1, Scheme 3, suitably substituted nitrobenzene of formula (10), wherein X is a suitable leaving group, such as Cl, F, Br, or triflate (OTf) is condensed with the [1,3'] pyrrolidinyl-pyrrolidine of formula (4) in order to form an intermediate of formula (11). Such condensation reactions can again be carried out using any of the procedures known to one skilled in the art. For example, such condensation reaction can be carried out in a polar solvent such as DMSO in the presence of a base such as potassium carbonate at ambient to super-ambient temperature conditions.

In step 2, Scheme 3, intermediate of formula (11) is reduced by hydrogenation or other known chemical methods, such as using tin dichloride in hydrochloric acid, to form the key intermediate (12).

Scheme 3

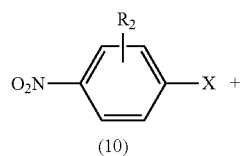

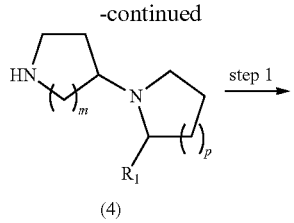

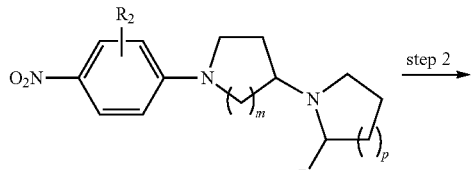

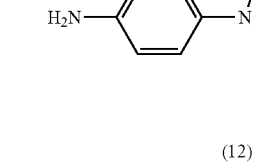

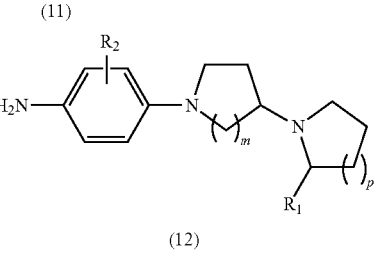

m, p = 1 or 2

Scheme 4 illustrates the preparation of compounds of formula (16). In step 1, Scheme 4, commercially available tetrahydro-pyran-4-carboxylic acid esters, such as methyl or ethyl esters, of formula (13) is treated with suitable base, such as nBuLi in presence of HMPA in THF, followed by alkenyl halides, to form intermediate of formula (15). This reaction can be carried out using any of the procedures known to one skilled in the art, such as reported in the literature (Nagumo, S.; Matoba A.; et al, Tetrahedron, 2002, 58(49), 9871-9877; Stafford, J. A.; Heathcock, C. H. J. Org. Chem., 1990, 55(20), 5433-5434). In step 2, Scheme 4, the alkene (15) is cleaved with $OsO_4$ and $NaIO_4$ in propanol and water to form aldehyde (16).

Scheme 4

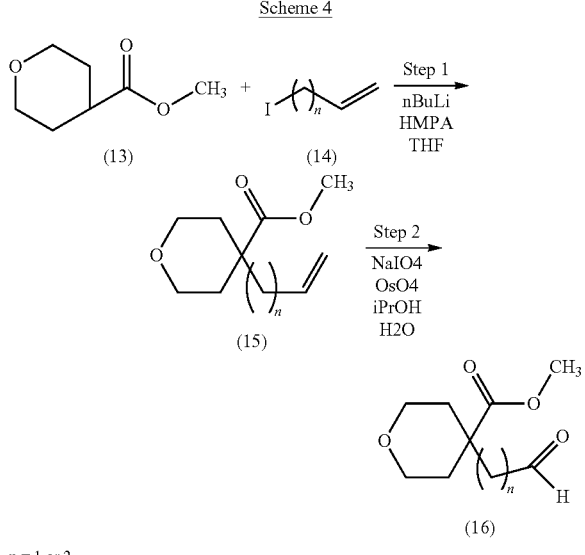

n = 1 or 2

The compounds of the present invention can be prepared by using the intermediates as prepared using the Schemes 1 to 4 and then employing either Method (A) or Method (B) as illustrated further below.

Scheme 5 illustrates the preparation of compounds of this invention using Method (A). In step 1, Scheme 5, the aldehyde of formula (16) is condensed with a desired intermediate of formula (12) by any of the known reductive amination procedures to form an intermediate of formula (17). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (17). The cyclization is then initiated by catalytic amount of base, such as potassium t-butoxide in aprotic solvents, such THF, to form compounds of formula (18).

condensed with a desired commercially available bromide of formula (19) by any of the known reductive amination procedures to form an intermediate of formula (20). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (20). The cyclization is then initiated by catalytic amount of base, such as potassium t-butoxide in aprotic solvents, such THF, to form compounds of formula (21). The intermediate of formula (21) is then condensed with the amine intermediate (4) or (9) prepared according to Schemes 6 and 7 to form the compounds of this invention (18).

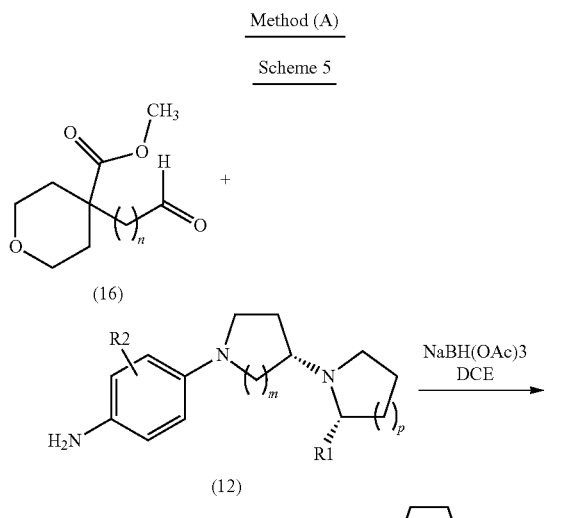
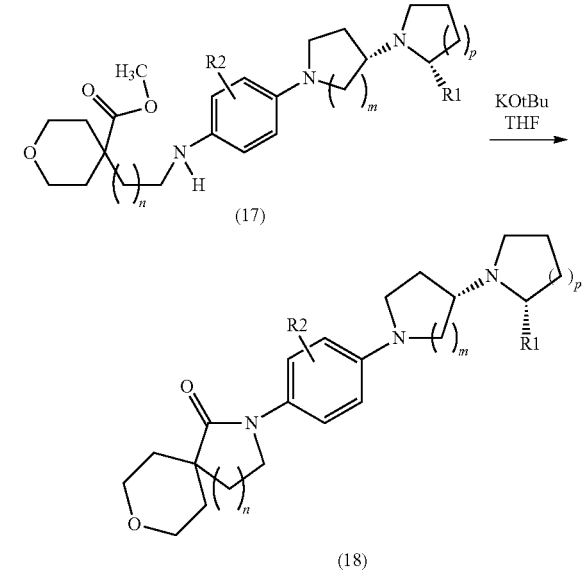
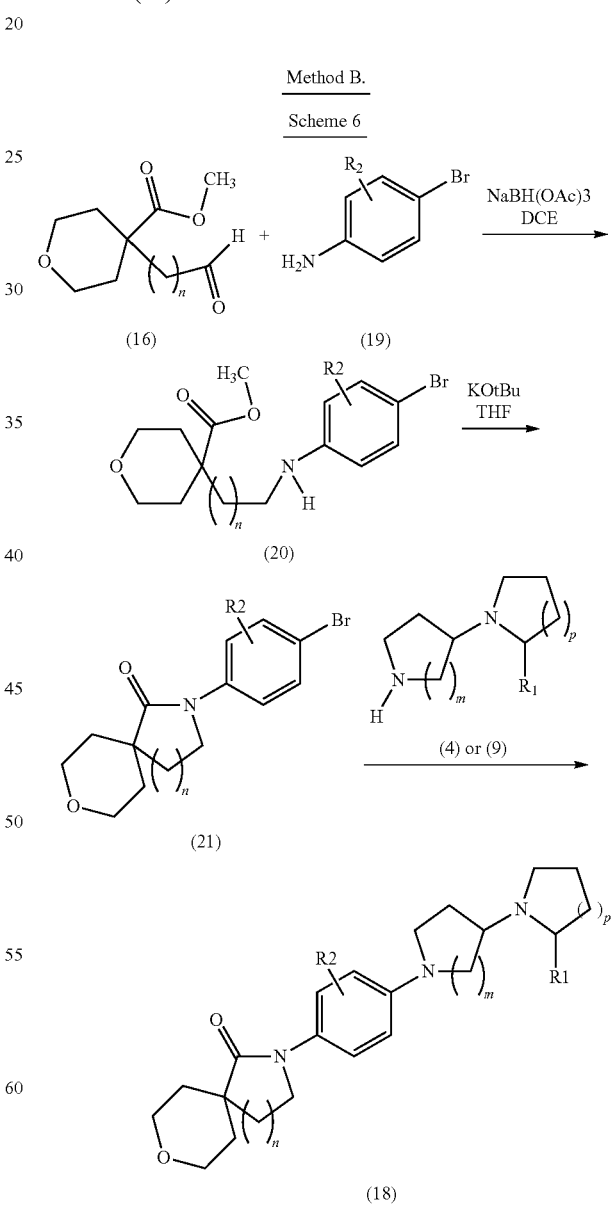

Schemes 6 and 7 illustrate the preparation of compounds of this invention by Method (B). The aldehyde of formula (16) is

Scheme 7

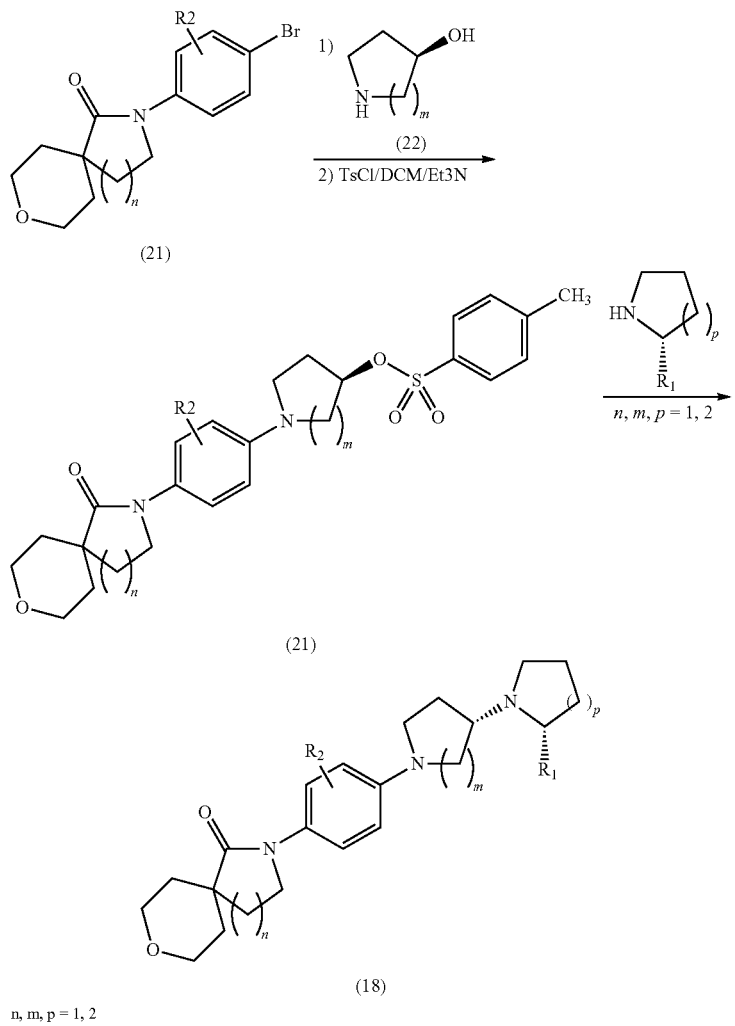

n, m, p = 1, 2

As already noted hereinabove, the compounds of this invention can readily be converted into salts. More particularly, the compounds of the present invention are basic, and as such compounds of this invention are useful in the form of the free base or in the form of a pharmaceutically acceptable acid addition salt thereof. Acid addition salts may be a more convenient form for use; and, in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

In another aspect of this embodiment, a specific disease, a disorder or a condition that can be prevented and/or treated with the compound of this invention include, without any limitation the following: sleep-related disorders (specific examples include without any limitation narcolepsy, attentional deficits, circadian rhythm sleep disorders, obstructive sleep apnea, periodic limb movement and restless leg syndrome, excessive sleepiness and drowsiness due to medication side-effect, etc.), neurological disorders (specific examples that may be enumerated include but not limited to dementia, Alzheimer's disease, multiple sclerosis, epilepsy and neuropathic pain), neuropsychological and cognitive disorders (a few of the specific examples include without any limitation include schizophrenia, attention deficit/hyperactivity disorder, Alzheimer's disease, depression, seasonal affective disorder, and cognitive impairment). Certain of the disorders also include cognitive impairment associated with schizophrenia (CIAS), anxiety disorders such as generalized anxiety, panic disorder and post-traumatic stress disorder, and major depressive disorder. Other disorders include dementia of Alzheimer type (DAT), cognitive deficits related to neurological diseases such as Alzheimer, Parkinson, Huntington, age related cognitive impairment, mild cognitive impairment, vascular dementia, Lewis Body dementia and any other cognition associated to cognitive deficits.

As described hereinbelow by way of specific examples, the compounds of formula (I) bind to the H3 receptors and demonstrate inverse agonism versus H3 functional activity. Therefore, the compounds of this invention may have utility in the treatment of diseases or conditions ameliorated with H3 receptor ligands. More specifically, the compounds of the present invention are H3 receptor ligands that modulate function of the H3 receptor by antagonizing the activity of the receptor. Further, the compounds of this invention may be inverse agonists that inhibit the basal activity of the receptor or they may be antagonists that completely block the action of receptor-activating agonists. Additionally, the compounds of this invention may also be partial agonists that partially block or partially activate the H3 receptor or they may be agonists that activate the receptor. Thus the compounds of this invention may act differentially as antagonists, inverse agonists and/or partial agonists depending on functional output, histamine tone and or tissue context. Accordingly, the differential activities of these compounds may allow for utility to ameliorate multiple disease states as specifically enumerated above.

Thus in one aspect of this invention there is provided a method of treating a disease in a patient, said disease selected from the group consisting of sleep related disorder, dementia, Alzheimer's disease, multiple sclerosis, cognitive disorder, attention deficit hyperactivity disorder and depression, comprising administering to said patient a therapeutically effective amount of a compound of formula (I).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of H3 receptors. That is, as noted above, the compounds of the present invention are modulators of H3 receptors and may be effectively administered to ameliorate any disease state which is mediated all or in part by H3 receptors.

All of the various embodiments of the compounds of this invention as disclosed herein can be used in the method of treating various disease states as described herein. As stated herein, the compounds used in the method of this invention are capable of inhibiting the effects of H3 receptor and thereby alleviating the effects and/or conditions caused due to the activity of H3.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

Finally, in yet another embodiment of this invention, there is also provided a pharmaceutical composition comprising a pharmaceutically acceptable carrier and a compound of formula (I), including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature H3 inhibitory activity and thus are useful in treating any disease, condition or a disorder caused due to the effects of H3 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES (GENERAL)

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "DMSO" refers to dimethyl sulfoxide, "DMF" refers to N,N-dimethylformamide, "CDI" refers to 1,1'-carbonyldiimidazole, "DCM" or "$CH_2Cl_2$" refers to dichloromethane, "DCE" refers to 1,2-dichloroethane, "HCl" refers to hydrochloric acid, "EtOAc" refers to ethyl acetate, "PBS" refers to Phosphate Buffered Saline, "IBMX" refers to 3-isobutyl-1-methylxanthine, "PEG" refers to polyethylene glycol, "MeOH" refers to methanol, "$MeNH_2$" refers to methyl amine, "$N_2$" refers to nitrogen gas, "iPrOH" refers to isopropyl alcohol, "$Et_2O$" refers to ethyl ether, "LAH" refers to lithium aluminum hydride, "heptane" refers to n-heptane, "HMBA-AM" resin refers to 4-hydroxymethylbenzoic acid amino methyl resin, "$PdCl_2(dppf)_2$" refers to 1,1'-bis(diphenylphosphino)ferrocene-palladium (II) dichloride DCM complex, "HBTU" refers to 2-(1H-benzotriazol-1yl)-1,1,3,3-tetramethyluronium hexafluorophosphate, "DIEA" refers to diisopropylethylamine, "CsF" refers to cesium fluoride, "MeI" refers to methyl iodide, "AcN," "MeCN" or "$CH_3CN$" refers to acetonitrile, "TFA" refers to trifluoroacetic acid, "THF" refers to tetrahydrofuran, "NMP" refers to 1-methyl-2-pyrrolidinone, "$H_2O$" refers to water, "BOC" refers to t-butyloxycarbonyl, "brine" refers to a saturated aqueous sodium chloride solution, "M" refers to molar, "mM" refers to millimolar, "M" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet, dd=doublet of doublets; br=broad; LC=liquid chromatograph; MS=mass spectrograph; ESI/MS=electrospray ionization/mass spectrograph; RT=retention time; M=molecular ion, "~"=approximately.

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1H$ NMR spectra are run at 300 MHz on a Gemini 300 or Varian Mercury 300 spectrometer with an ASW 5 mm probe, and usually recorded at ambient temperature in a deuterated solvent, such as $D_2O$, DMSO-$D_6$ or $CDCl_3$ unless otherwise noted. Chemical shifts values ( ) are indicated in parts per million (ppm) with reference to tetramethylsilane (TMS) as the internal standard.

High Pressure Liquid Chromatography-Mass Spectrometry (LCMS) experiments to determine retention times ($R_T$) and associated mass ions are performed using one of the following methods:

Mass Spectra (MS) are recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 µM, 1 ml/min MUX: Column: YMC Jsphere 33×2, 1 ml/min
Grad (AcN+0.05% TFA):(H2O+0.05% TFA)=5:95 (0 min) to 95:5 (3.4 min) to 95:5 (4.4 min).

LCT2: YMC Jsphere 33×2 4 µM, (AcN+0.05% TFA): (H2O+0.05% TFA)=5:95 (0 min) to 95:5 (3.4 min) to 95:5 (4.4 min)

QU: YMC Jsphere 33×2 1 ml/min, (AcN-F0.08% formic acid):(H2O+0.1')/0 formic acid)=5:95 (0 min) to 95:5 (2.5 min) to 95:5 (3.0 min)

The following examples describe the procedures used for the preparation of various starting materials employed in the preparation of the compounds of this invention.

INTERMEDIATES

Intermediate (i)

2-Methyl-[1,3']bipyrrolidinyl-1'-carboxylic acid tert-butyl ester

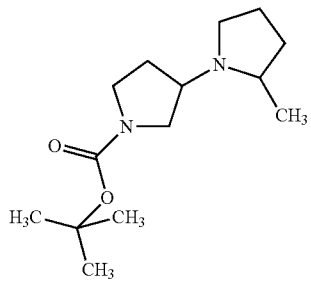

To a solution of N-BOC-3-pyrrolidinone (4.22 g, 22.9 mmol) and 2-methylpyrroline (1.95 g, 22.9 mmol) (HCl salt was made by addition of 22.9 mL of 1 M HCl in ether into the DCM solution of 2-methylpyrroline, then evaporated) in DCE (60 mL) was added powdered sodium triacetoxyborohydride slowly under $N_2$ at r.t. The yellowish milky solution was stirred at r.t. overnight. LC/MS—m/z 255 and 199 (base and M-tBu).

The reaction was quenched with aq. $NaHCO_3$ solution (100 mL). The two layers were separated, and the aqueous layer was extracted with DCM (20 mL×2). The combined DCM extracts were washed with sodium bicarbonate (10 mL), and brine (5 mL×2), dried (anhydrous potassium carbonate), filtered, and concentrated in vacuo. The crude product was purified on a silica gel column, eluted with DCM and 7.5% MeOH in DCM to get 5.50 g (yield: 94%) of the title compound as a liquid. MS: 255 (M+H⁺); TLC: 0.5 (10% MeOH in DCM).

Intermediate (ii)

2-Methyl-[1,3']bipyrrolidinyl hydrochloride

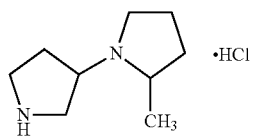

2-Methyl-[1,3']bipyrrolidinyl-1'-carboxylic acid tert-butyl ester (5.50 g, 21.62 mmol) was treated with 20 mL of 4 M HCl in dioxane at 0° C. The solution was stirred under nitrogen at r.t. overnight. TLC (10% MeOH in DCM) did not detect the starting material. N$_2$ was passed through the solution with stirring. The outlet was passed through KOH solution to absorb HCl for 30 min. The solvent was removed by evaporation to dryness to get the title compound as a hygroscopic gummy material, 5.3 g (~100%). This material was used without further purification in subsequent steps as illustrated below. LCMS: R$_T$=0.35 minutes, MS: 155 (M+H).

$^1$H NMR (D$_2$O, 300 MHz): δ 4.30 (m), 3.85 (m), 3.76 (s), 3.5 (m), 3.46 (m), 3.32 (m), 2.66 (m), 2.28 (m), 2.10 (m), 1.46 (bs).

Intermediate (iii)

4-(2-Propyl-pyrrolidin-1-yl)-piperidine

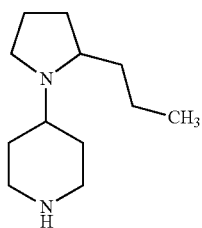

This intermediate is synthesized essentially in the same way as described in the synthesis of 2-methyl-[1,3']bipyrrolidinyl hydrochloride from 1.6 g of the ketone to obtain 1.48 g (94% yield) of the title product as a clear oil.

LC/MS: R$_T$=3.42 min.; MS: 197.19 (M+H)

NMR: $^1$H NMR (300 MHz CDCl$_3$) δ 4.72 (1H, br), 3.28 (1H, d, J=12.65 Hz), 3.04 (2H, m), 2.86-2.53 (4H, m), 2.05-1.47 (10H, m), 1.47 (3H, m), 0.93 (3H, m)

Intermediate (iv)

4-(2-Isopropyl-pyrrolidin-1-yl)piperidine

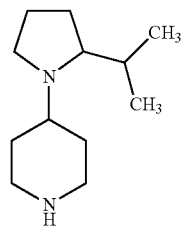

This intermediate is synthesized essentially in the same way as described in the synthesis of 2-methyl-[1,3']bipyrrolidinyl hydrochloride from 1.6 g of the ketone to obtain 1.57 g (100% yield) of the title product as a clear oil.

LC/MS: R$_T$=3.69 min.; MS: 197.19 (M+H)

NMR: 1H NMR (300 MHz CDCl3) δ: 5.77 (1H, br), 3.35 (1H, m), 2.98 (2H, m), 2.84-2.46 (4H, m), 2.05-1.46 (10H, m), 0.86 (6H, dt, J=10.40, 6.05 Hz)

Intermediate (v)

4-(2-Methoxymethyl-pyrrolidin-1-yl)-piperidine

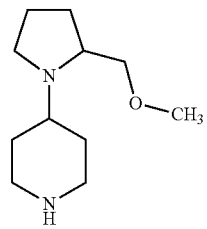

This intermediate is synthesized essentially in the same way as described in the synthesis of 2-Methyl-[1,3']bipyrrolidinyl hydrochloride from 1.6 g of the ketone to get 1.40 g (89% yield) of the title product as a clear oil.

LC/MS: 199 (M+H)

Intermediate (vi)

2-Propyl-[1,3']bipyrrolidinyl

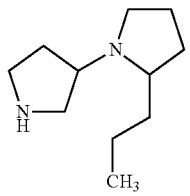

This intermediate is synthesized essentially in the same way as described in the synthesis of 2-Methyl-[1,3']bipyrrolidinyl hydrochloride from 1.48 g of the ketone to get 1.46 g (100% yield) of the title product as a clear oil.

LC/MS: R$_T$=3.64 min.; MS: 183.18 (M+H)

NMR: $^1$H NMR (300 MHz, CDCl3) δ: 3.39 (1H, m), 3.17 (1H, m), 2.94 (3H, m), 2.69-2.40 (4H, m), 2.13-1.10 (10H, m), 0.92 (3H, m)

Intermediate (vii)

2-Isopropyl-[1,3']bipyrrolidinyl

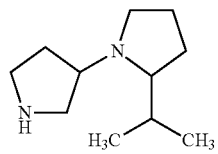

This intermediate is synthesized essentially in the same way as described in the synthesis of 2-Methyl-[1,3']bipyrrolidinyl hydrochloride from 1.48 g of the ketone to obtain 1.46 g (100% yield) of the title product as a clear oil.

LC/MS: R$_T$=0.45 min.; MS: 183.19 (M+H)

NMR: 1H NMR (300 MHz, CDCl3) δ: 3.39 (1H, m), 3.17 (1H, m), 3.05-2.74 (3H, m), 2.69-2.36 (3H, m), 2.10-1.69 (3H, m), 1.63 (4H, m), 0.84 (6H, m)

Intermediate (viii)

2-Methoxymethyl-[1,3']bipyrrolidinyl

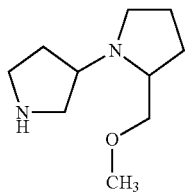

This intermediate is synthesized essentially in the same way as described in the synthesis of 2-Methyl-[1,3']bipyrrolidinyl hydrochloride from 1.48 g of the ketone to obtain 1.47 g (100% yield) of the title product as a clear oil.

LC/MS: $R_T$=0.42 min.; MS: 185.16 (M+H)

NMR: 1H NMR (300 MHz, CDCl3) δ: 3.38 (6H, m), 3.21 (2H, m), 3.06-2.40 (6H, m), 2.14-1.57 (5H, m)

Intermediate (ix)

4-(2-Ethyl-pyrrolidin-1-yl)piperidine

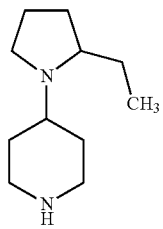

This intermediate is synthesized essentially in the same way as described in the synthesis of 2-Methyl-[1,3']bipyrrolidinyl hydrochloride from 912 mg of the ketone to get 800 mg (96% yield) of the title product as a clear oil.

LC/MS: $R_T$=3.57 min.; MS: 183.18 (M+H)

NMR: 1H NMR (300 MHz, CDCl3) δ: 3.19-2.76 (4H, m), 2.57 (4H, m), 2.15-1.20 (10H, m), 1.19 (1H, m), 0.86 (3H, t, J=7.51 Hz)

Intermediate (x)

2-Ethyl-[1,3']bipyrrolidinyl

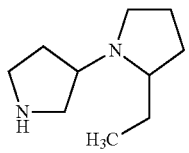

This intermediate is synthesized essentially in the same way as described in the synthesis of 2-Methyl-[1,3']bipyrrolidinyl hydrochloride from 848 mg of the ketone to obtain 750 mg (97% yield) of the title product as a clear oil.

LC/MS: $R_T$=3.64 min.; MS: 169.16 (M+H)

$^1$H NMR (300 MHz, CDCl3) δ:3.11-2.29 (8H, m), 2.19-1.11 (9H, m), 0.87 (3H, t, J=7.51 Hz)

Intermediate (xi)

2-Methyl-1'-(3-methyl-4-nitro-phenyl)-[1,3']bipyrrolidinyl

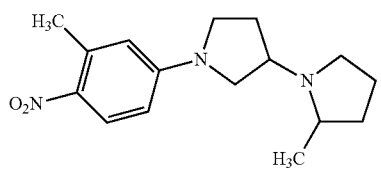

2-Methyl-[1,3']bipyrrolidinyl hydrochloride (Intermediate (ii) obtained above, 5.3 g, 21.6 mmol, 1.12 equiv.) was dissolved in anhydrous DMSO (30 mL). To this solution was added 5-fluoro-2-nitrotoluene (3.00 g, 18.78 mmol, 1 equiv.), followed by powdered potassium carbonate (8.9 g, 65 mmol). The suspension was heated on an oil bath to 85° C. for 4 h when the starting material was consumed as determined by TLC (5% MeOH in DCM) and LC/MS. To the suspension were added 20 mL of water and 50 mL of DCM. The two layers were separated, and the aqueous layer was extracted with DCM (20 mL×2). The combined DCM extracts were washed with sodium bicarbonate (20 mL), and brine (15 mL×2), dried (anhydrous potassium carbonate), filtered, and concentrated in vacuo. The crude product was purified on a silica gel column, eluted with 5% MeOH in DCM to get the title compound as a yellow solid after drying, 5.47 g (100%). MS: 290 (M+H$^+$).

$^1$H NMR (300 MHz, CDCl$_3$), δ (ppm): 8.10 (d, 9 Hz, 1H), 6.36 (bd, 9 Hz, 1H), 6.28 (bs, 1H), 3.4-3.2 (m, 5H), 3.00-2.78 (m, 2H), 2.64 (s, 3H), 1.7-2.2 (m, 6H), 1.5 (m, 1H), 1.06 (m, 3H).

Intermediate (xii)

4-(2-Methyl-[1,3']bipyrrolidinyl-1'-yl)-phenylamine

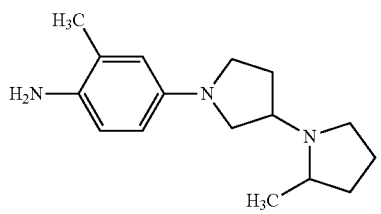

A solution of 2-methyl-1'-(3-methyl-4-nitro-phenyl)-[1,3'] bipyrrolidinyl (Intermediate (iii) obtained above, 2.23 g, 7.7 mmol) in MeOH was de-aerated and nitrogen was introduced. To this solution was added Pd—C (10%). This mixture was stirred under H$_2$ atmosphere at r.t. for 8 h. TLC (10% MeOH in DCM) and LC/MS showed the reaction was complete. The mixture was passed through a Celite pad, rinsed with methanol. The filtrate was concentrated to dryness, and further dried under high vacuum to yield a reddish brown liquid after drying under high vacuum to obtain the title compound as a gummy black liquid, 1.73 g (86%). This material was used in the next step without further purification and storage. MS: 260 (M+H+).

Intermediate (xiii)

(R)-3-(Toluene-4-sulfonyloxy)-pyrrolidine-1-carboxylic acid tert-butyl ester

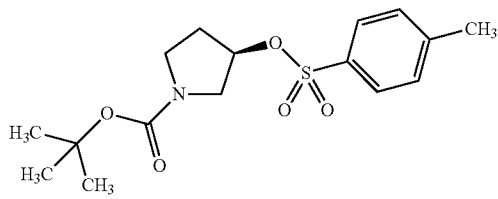

To a 2 L round-bottom flask equipped with a mechanical stirring rod and a 250 ml addition funnel was added p-tosyl chloride (58 g, 305 mmol, 1.5 eq) and 600 ml of anhydrous DCM. The solution was cooled with ice-water bath. $Et_3N$ (65 ml) and DMAP (2.65 g) were added. A solution of (R)-3-(−)-N-Boc-hydroxy pyrrolidine (38 g, 203 mmol, 1.0 eq) in 200 ml of DCM was added slowly. The reaction mixture was allowed to stir at room temperature over night. TLC showed completion of the reaction. The product had an $R_f$ value of 0.3 (TLC developed in DCM). The reaction was cooled by ice-water bath. Polymer-supported trisamine (32 g) was added and stirred for 30 min. Trisamine bead was filtered and rinsed with 300~400 mL of DCM. The organic solution was washed with 200 mL of $H_3PO_4$ (1M) solution twice, followed by saturated $NaHCO_3$ solution (200 mL), and brine (200 mL). The organic phase was dried over $K_2CO_3$. After concentration, the crude product was purified by a 750 g silica gel cartridge (DCM to 5% MeOH in DCM) to afford the title compound as a beige oil (52 g, 75%).

MS: 363 (M+Na$^+$); TLC (DCM) Rf=0.3.

$^1$H NMR (CDCl$_3$, 300 MHz), δ (ppm): 7.80 (d, 9.0 Hz, 2H), 7.35 (d, 7.8 Hz, 2H), 5.04 (bs, 1H), 3.45 (m, 4H), 2.46 (bs, 3H), 2.05 (m, 2H), 1.43 (s, 9H).

Intermediate (xiv)

(S)-3-(Toluene-4-sulfonyloxy)-pyrrolidine-1-carboxylic acid tert-butyl ester

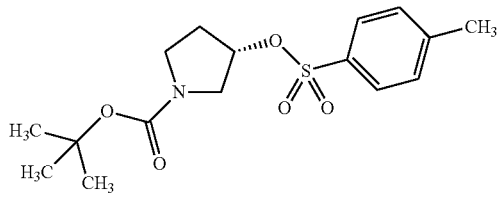

A round bottomed flask was charged with 80 mL of anhydrous DCM. The solvent was evacuated and purged with nitrogen. To this solvent was added (3S)-1-BOC-3-pyrrolidinol (obtained from Astatech), (16.32 g, 33.8 mmol), DMAP (0.4 g). The solution was cooled to an ice-water bath. To this cold solution was added a solution of p-toluene-sulfonyl chloride (9.67 g, 50.87 mmol, 1.5 equiv.) in 20 mL of DCM. The ice-water bath was removed and the solution was stirred under nitrogen overnight. TLC (5% MeOH in DCM for SM, I2 visualization; DCM for product, UV) showed the completion of the reaction. The reaction was quenched by addition of polymer-supported amine (4.5 g), stirred 30 min. 50 mL of DCM was added and filtered. The filtration pad was washed with DCM. The organic was washed with $H_3PO_4$ (1M, 2×50 mL), followed by NaHCO$_3$ (50 mL, brine (50 mL), dried ($K_2CO_3$), filtered and concentrated to a liquid. This was purified on a 110 g silica gel column on Analogix using 0-2% MeOH in DCM to obtain pure product, 8.82 g (77% yield).

TLC (DCM) Rf=0.3. LC: Rt=3.55 min, 100% pure based on total ion, MS: 363 (M+Na); 342, 327, 286 (base).

$^1$H NMR (300 MHz, CDCl$_3$), δ (ppm): 7.81 (d, 8.7 Hz, 2H), 7.37 (d, 8.7 Hz, 2H), 5.04 (bs, 1H), 3.45 (m, 4H), 2.46 (s, 3H), 1.44 (s, 9H).

Intermediate (xv)

(2S,3'S)-2-Methyl-[1,3']bipyrrolidinyl-1'-carboxylic acid tert-butyl ester

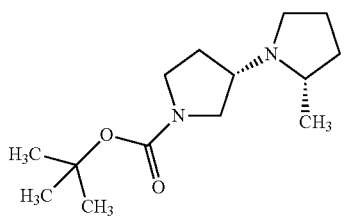

The tosylate (52 g, 0.15 mol, 1.0 eq), (2S)-2-methyl pyrrolidine (25.2 g, 0.3 mol, 2.0 eq), anhydrous CH$_3$CN (500 ml), and dry K$_2$CO$_3$ powder (50 g, 36 mmol, 2.4 eq) were added to a 2 L round-bottom flask equipped with a mechanical stirrer and a reflux condenser. The resulting suspension was stirred at 75° C. for 20 h. The heating block was set at 88° C.

LC/MS showed a small amount of starting material at m/z 363. The reaction mixture was concentrated in vacuo. The residue was partitioned between 200 mL of water and 400 mL of DCM. The aqueous layer was washed with 50 mL of DCM twice. The organic extracts were combined and washed with 150 mL of saturated NaHCO$_3$ solution, 150 mL of brine, and dried over K$_2$CO$_3$. The crude was purified by silica gel column, eluted with 5-10% MeOH in DCM. The product still had weak UV absorption at 254 nm and 280 nm. A pale yellow oil was obtained. Yield: 24.5 g (64%).

LCMS: $R_T$=1.27 minutes, MS: 255 (M+H).

$^1$H NMR (300 MHz, CDCl$_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (xvi)

(2R,3'S)-2-Methyl-[1,3']bipyrrolidinyl-1'-carboxylic acid tert-butyl ester

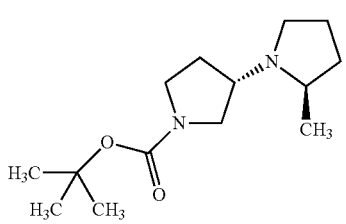

The title compound was prepared in a manner substantially the same as intermediate (2R,3'S)-2-Methyl-[1,3']bipyrrolidinyl-1'-carboxylic acid tert-butyl ester by condensing 3-(3R)-(toluene-4-sulfonyloxy)-pyrrolidine-1-carboxylic acid tert-butyl ester with R-(−)-2-methylpiperindine (obtained from Advanced Asymmetrics). LCMS: $R_T$=1.05 minutes, MS: 255 (M+H).

¹H NMR (300 MHz, CDCl₃), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (xvii)

(2S,3'R)-2-Methyl-[1,3']bipyrrolidinyl-1'-carboxylic acid tert-butyl ester

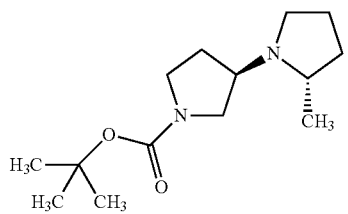

3-(3S)-(Toluene-4-sulfonyloxy)-pyrrolidine-1-carboxylic acid tert-butyl ester (6.82 g, 19.97 mmol, 1 equiv.) and S-(+)-2-methyl-piperindine (obtained from Advanced Asymmetrics), (3.40 g, 40 mmol, 2 equiv.) were dissolved in anhydrous CH₃CN (65 mL). To this colorless solution was added powder K₂CO₃ (powder, 325 mess, 98+%, 6.10 g, 44.2 mmol, 2.2 equiv.) at r.t. The suspension was heated with stirring under nitrogen over an oil bath maintained at 80° C. for 24 h. TLC (3% MeOH in DCM for SM, 7.5% MeOH in DCM for product) showed the SM was consumed almost completely. LC/MS showed very little amount of starting material at m/z 363.

The suspension was concentrated to dryness. The residue was taken in water (25 mL) and DCM (80 mL). The two layers were separated, and the aqueous layer was extracted with DCM (20 mL×2). The combined DCM extracts were washed with sodium bicarbonate (25 mL), and brine (25 mL), dried (anhydrous potassium carbonate), filtered, and concentrated in vacuo. The crude product was purified on a silica gel column (70 g) on Analogix, eluted with MeOH in DCM (0 to 7.5%) to obtain 4.08 g (80.3%) of the title compound as a gummy material. LCMS: $R_T$=1.14 minutes, MS: 255 (M+H).

¹H NMR (300 MHz, CDCl₃), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (xviii)

(2R,3'R)-2-Methyl-[1,3']bipyrrolidinyl-1'-carboxylic acid tert-butyl ester

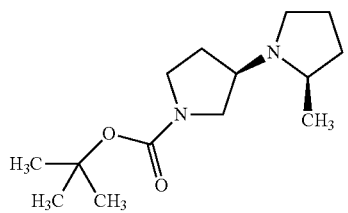

The title compound was prepared in a manner substantially the same as intermediate (2R,3'S)-2-Methyl-[1,3']bipyrrolidinyl-1'-carboxylic acid tert-butyl ester by condensing 3-(3S)-(toluene-4-sulfonyloxy)-pyrrolidine-1-carboxylic acid tert-butyl ester and R-(−)-2-methylpiperindine (obtained from Advanced Asymmetrics). LCMS: $R_T$=1.09 minutes, MS: 255 (M+H).

¹H NMR (300 MHz, CDCl₃), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (xix)

(S)-3-((S)-2-Methyl-piperidin-1-yl)-pyrrolidine-1-carboxylic acid tert-butyl ester

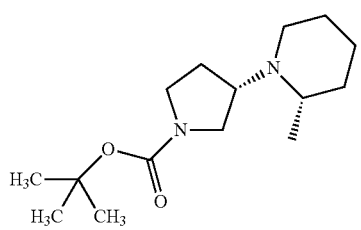

The title compound was prepared in a manner substantially the same as intermediate (2R,3'S)-2-Methyl-[1,3']bipyrrolidinyl-1'-carboxylic acid tert-butyl ester by condensing 3-(3R)-(toluene-4-sulfonyloxy)-pyrrolidine-1-carboxylic acid tert-butyl ester (5 g) with (S)-2-Methyl-piperidine to get 1.50 g (38% yield) of the product as a beige oil.

LC/MS: $R_T$=1.95 mins. MS: 269.

Intermediate (xx)

4-((S)-2-Methyl-pyrrolidin-1-yl)-piperidine-1-carboxylic acid tert-butyl ester

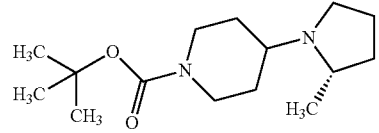

The title compound was prepared in a manner substantially the same as intermediate (2R,3'S)-2-Methyl-[1,3']bipyrrolidinyl-1'-carboxylic acid tert-butyl ester by condensing 4-(Toluene-4-sulfonyloxy)-piperidine-1-carboxylic acid tert-butyl ester with (S)-(−)-2-methylpiperindine to get 2.60 g (97% yield) of the product as a pale yellow oil.

LC/MS: $R_T$=2.13 mins. MS: 269.

Intermediate (xxi)

(2S,3'R)-2-Methyl-[1,3']bipyrrolidinyl dihydrochloride

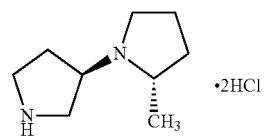

2(2S)-Methyl-[1,3'(3'R)]bipyrrolidinyl-1'-carboxylic acid tert-butyl ester (7.91 g, 31.14 mmol) was treated with 28.8 mL of HCl in dioxane at 0° C. The solution was stirred under nitrogen at r.t. overnight. Both TLC (10% MeOH in DCM) and LC/MS did not detect the starting material. N$_2$ was passed through the solution with stirring. The outlet was passed through KOH solution to absorb HCl for 1 h. The solvent was removed by evaporation to dryness to get the title compound as a hygroscopic very thick gummy (2HCl salt, hydrated—Exact composition unknown), 8.07 g (~100%). MS: 155 (M+H).

$^1$H NMR: (D$_2$O, 300 MHz), δ (ppm): 11.6 (bs, 1H), 9.1 (bs, 1H) 4.12 (m, 1H) 3.5 (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xxii)

(2S,3'S)-2-Methyl-[1,3']bipyrrolidinyl dihydrochloride

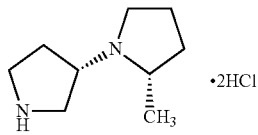

(2S,3'S)-2-Methyl-[1,3']bipyrrolidinyl-1'-carboxylic acid tert-butyl ester (24.5 g) was dissolved in 30 ml of dry 1,4-dioxane. HCl solution (85 ml, 4M in dioxane) was added at 0° C., and allowed to stir at room temperature. Brown gum appeared after about 20 minutes. After 4 h, the reaction was complete. N$_2$ was passed through the flask for 1 h with stirring. The outlet passed though KOH solution to absorb HCl. The solvent was removed by vacuum to afford 29 g of hygroscopic beige gum.

LCMS: R$_T$=0.37 minutes, MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xxiii)

(2R,3'S)-2-Methyl-[1,3']bipyrrolidinyl dihydrochloride

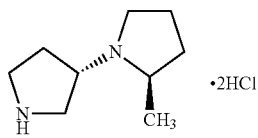

The title compound was prepared in a manner substantially the same as intermediate (2S,3'R)-2-Methyl-[1,3']bipyrrolidinyl dihydrochloride by acid hydrolysis of 2(2R)-methyl-[1,3'(3'S)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5 (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xxiv)

(2R,3'R)-2-Methyl-[1,3']bipyrrolidinyl dihydrochloride

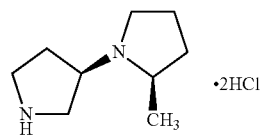

The title compound was prepared in a manner substantially the same as intermediate (2S,3'R)-2-Methyl-[1,3']bipyrrolidinyl dihydrochloride by acid hydrolysis of 2-(2R)-methyl-[1,3'(3'R)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xxv)

4-((S)-2-Methyl-pyrrolidin-1-yl)piperidine

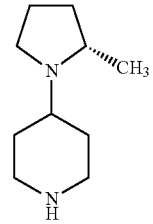

The title compound was prepared in a manner substantially the same as intermediate (2S,3'R)-2-Methyl-[1,3']bipyrrolidinyl dihydrochloride by acid hydrolysis of BOC-4-((S)-2-Methyl-pyrrolidin-1-yl)piperidine which was synthesized by condensation of tosylate with (S)-(−)-2-methylpyrrolidine to get 1.28 g (95% yield) of the title product as a clear oil.

LC/MS: 3.6 min.; MS: 169.17 (M+H)

$^1$H NMR (300 MHz CDCl3) δ (ppm): 3.12 (2H, m), 2.88 (2H, m), 2.59 (4H, m), 2.02-1.59 (6H, m), 1.59-1.31 (3H, m), 1.05 (3H, d, J=6.05 Hz)

Intermediate (xxvi)

(S)-2-Methyl-[1,4']bipiperidinyl

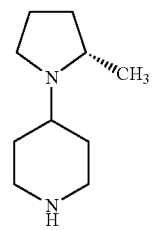

The title compound was prepared in a manner substantially the same as intermediate (2S,3'R)-2-Methyl-[1,3']bipyrrolidinyl dihydrochloride by acid hydrolysis of BOC-(S)-2-

Methyl-[1,4']bipiperidinyl which was synthesized by condensation of corresponding tosylate with (S)-(−)-2-methylpiperindine to get 1.37 g (94% yield) of the title product as a clear oil.

LC/MS: $R_T$=3.82 min.; MS: 183 (M+H)

$^1$H NMR (300 MHz CDCl3) δ (ppm): 3.11 (2H, m), 2.86 (2H, m), 2.58 (4H, m), 2.17 (1H, m), 1.91 (1H, m) 1.66 (5H, m), 1.51-1.20 (4H, m), 1.07 (3H, d, J=6.23 Hz)

Intermediate (xxvii)

(2S,3'R)-2-Methyl-1'-(3-methyl-4-nitro-phenyl)-[1,3']bipyrrolidinyl

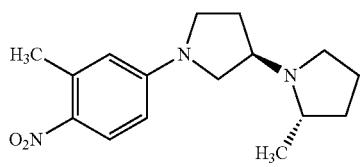

2(2S)-Methyl-[1,3'(3'R)]bipyrrolidinyl (0.23 g, 1.2 mmol) was dissolved in anhydrous DMSO (5 mL) in a flask. To this solution was added 5-fluoro-2-nitrotoluene (223 mg, 1.44 mmol), followed by powdered anhydrous potassium carbonate (662 mg, 4.8 mmol). The suspension was heated on an oil bath to 85° C. for 4 h when the starting material was consumed as shown by TLC (5% MeOH/DCM) and LC/MS. MS: 290 (base peak).

To the suspension were added 2 mL of water and 5 mL of DCM. The two layers were separated, and the aqueous layer was extracted with DCM (10 mL×2). The combined DCM extracts were washed with sodium bicarbonate (5 mL), and brine (5 mL×2), dried (anhydrous potassium carbonate), filtered, and concentrated in vacuo. The crude product was purified on a silica gel column, eluted with 5% MeOH in DCM to get the title compound as a yellow solid after drying.

LCMS: $R_T$=1.38 minutes, MS: 290 (M+H).

$^1$H NMR (300 MHz, CDCl$_3$), δ (ppm): 8.10 (d, 9.1 Hz, 1H), 6.36 (dd, 9.2, 2.5 Hz, 1H), 6.28 (d, 2.4 Hz, 1H), 3.654 (m, 2H), 3.37 (m, 3H), 2.99 (dt, 3.7 Hz, 8.8 Hz, 1H), 2.84 (sixtet, 6.6 Hz, 1H), 2.65 (s, 3H), 2.56 (q, 8.1 Hz, 1H), 2.31 (m, 2H), 2.11 (m, 2H) 1.87 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results obtained were as follows: $R_T$=10.92 min; ee 99%

Intermediate (xxviii)

2-(2S)-Methyl-1'-(3-methyl-4-nitro-phenyl)-[1,3'(3'S)]bipyrrolidinyl

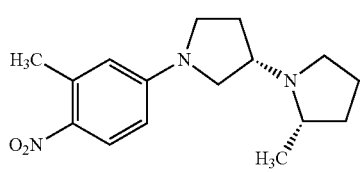

The title compound was prepared in a manner substantially the same as above by condensing 2(2S)methyl-[1,3'(3S)]bipyrrolidinyl and 5-fluoro-2-nitrotoluene.

LCMS: $R_T$=1.43 minutes, MS: 290 (M+H).

$^1$H NMR (300 MHz, CDCl$_3$), δ (ppm): 8.10 (d, 9.2 Hz, 1H), 6.36 (dd, 9.2, 2.8 Hz, 1H), 6.28 (d, 2.2 Hz, 1H), 3.6 (m, 2H), 3.3 (m, 3H), 3.00-2.78 (dt, 3.5 Hz, 8.8 Hz, 2H), 2.79 (m, 1H), 2.64 (s, 3H), 2.56 (m, 1H), 2.03 (m, 2H), 1.98 (m, 2H) 1.45 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results used were as follows: $R_T$=8.16 min; ee 100%.

Intermediate (xxix)

2-(2R)-Methyl-1'-(3-methyl-4-nitro-phenyl)-[1,3'(3'S)]bipyrrolidinyl

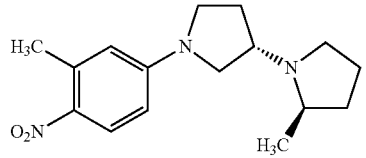

The title compound was prepared in a manner substantially the same as above by condensing 2(2R)-methyl-[1,3'(3'S)]bipyrrolidinyl and 5-fluoro-2-nitrotoluene.

LCMS: $R_T$=1.41 minutes, MS: 290 (M+H).

$^1$H NMR (300 MHz, CDCl$_3$), δ (ppm): 8.10 (d, 9.1 Hz, 1H), 6.36 (dd, 9.2, 2.5 Hz, 1H), 6.28 (d, 2.4 Hz, 1H), 3.654 (m, 2H), 3.37 (m, 3H), 2.99 (dt, 3.7 Hz, 8.8 Hz, 1H), 2.84 (sixtet, 6.6 Hz, 1H), 2.65 (s, 3H), 2.56 (q, 8.1 Hz, 1H), 2.31 (m, 2H), 2.11 (m, 2H) 1.87 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results used were as follows: $R_T$=11.93 min; ee 100%.

Intermediate (xxx)

2-(2R)-Methyl-1'-(3-methyl-4-nitro-phenyl)-[1,3'(3'R)]bipyrrolidinyl

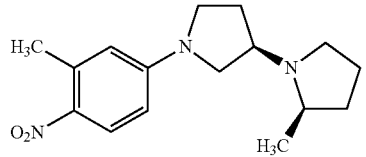

The title compound was prepared in a manner substantially the same as above by condensing 2(2R)-Methyl-[1,3'(3'R)]bipyrrolidinyl and 5-fluoro-2-nitrotoluene.

LCMS: $R_T$=1.43 minutes, MS: 290 (M+H).

$^1$H NMR (300 MHz, CDCl$_3$), δ (ppm): 8.10 (d, 9.2 Hz, 1H), 6.36 (dd, 9.2, 2.8 Hz, 1H), 6.28 (d, 2.2 Hz, 1H), 3.6 (m, 2H), 3.3 (m, 3H), 3.00-2.78 (dt, 3.5 Hz, 8.8 Hz, 2H), 2.79 (m, 1H), 2.64 (s, 3H), 2.56 (m, 1H), 2.03 (m, 2H), 1.98 (m, 2H) 1.45 (m, 1H), 1.08 (d, 6.2 Hz, 3H).

The analytical chiral HPLC conditions used were as follows: Isocratic 100% isopropanol with 0.5% IPAmine 5 ml/min outlet pressure 150 bar, 200 nM. The results used were as follows: $R_T$=8.95 min; ee 100%.

Intermediate (xxxi)

2-Methyl-4-(2-(2S)-methyl-[1,3'(3'R)]bipyrrolidinyl-1'-yl)-phenylamine

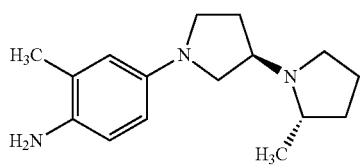

A solution of 2-(2S)-methyl-1'-(3-methyl-4-nitro-phenyl)-[1,3'(3'R)]bipyrrolidinyl (2.02 g, 6.98 mmol) in MeOH (40 mL) was de-aerated and nitrogen was introduced. To this solution was added Pd—C (10%, 0.2 g). This mixture was stirred under $H_2$ atmosphere at r.t. for 4 h. TLC (10% MeOH in DCM) and LC/MS showed the reaction was complete, and the product was detected by MS at 261. The mixture was passed through a Celite pad, rinsed with methanol. The filtrate was concentrated to dryness, and further dried to yield the title compound as a reddish brown liquid after drying under high vacuum, 1.81 g (100%). LC/MS: 260, TLC (10% MeOH/DCM): 0.3 Rf.

Intermediate (xxxii)

2-Methyl-4-(2-(2S)-methyl-[1,3'(3'S)]bipyrrolidinyl-1'-yl)-phenylamine

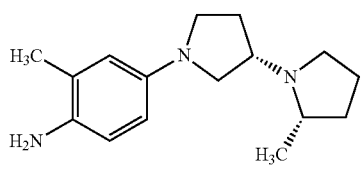

The title compound was prepared in a manner substantially the same as intermediate (xxiii) by hydrogenation of 2-(2S) Methyl-1'-(3-methyl-4-nitro-phenyl)-[1,3'(3'S)]bipyrrolidinyl. LC/MS: 260, TLC (10% MeOH/DCM): 0.3 Rf.

Intermediate (xxxiii)

2-Methyl-4-(2-(2R)-methyl-[1,3'(3'S)]bipyrrolidinyl-1'-yl)-phenylamine

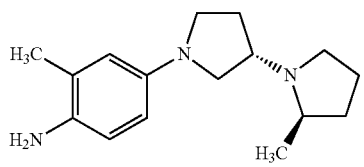

The title compound was prepared in a manner substantially the same as intermediate (xxiii) by hydrogenation of 2-(2R)-methyl-1'-(3-methyl-4-nitro-phenyl)-[1,3'(3'S)]bipyrrolidinyl. LC/MS: 260, TLC (10% MeOH/DCM): Rf=0.3.

Intermediate (xxxiv)

2-Methyl-4-(2(2R)-methyl-[1,3'(3'R)]bipyrrolidinyl-1'-yl)-phenylamine

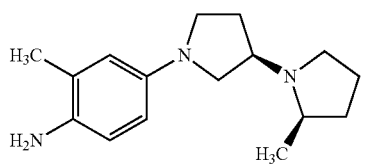

The title compound was prepared in a manner substantially the same as intermediate (xxiii) by hydrogenation of 2-(2R)-Methyl-1'-(3-methyl-4-nitro-phenyl)-[1,3'(3'R)]bipyrrolidinyl. LC/MS: 260, TLC (10% MeOH/DCM): Rf=0.3.

Intermediate (xxxv)

4-Allyl-tetrahydro-pyran-4-carboxylic acid methyl ester

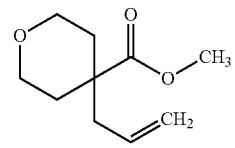

In a 250-mL RBF was weighed 6.1 g (60 mmol) of diisopropylamine and dissolved in THF (100 mL). This solution was cooled to −78° C. To this was added 37.5 mL of 1.6M butyllithium in hexane, stirred for 15 min, warmed up to 0° C. for 20 min, re-cooled to −78° C.

To this was added tetrahydro-pyran-4-carboxylic acid methyl ester (7.2 g, 50 mmol) in THF (10 mL). There was almost no color change (light a little bit). This was stirred at −78° C. for 45 min. Then, a mixture of 5 g of HMPA and 10.92 g of allyl iodide was added via canula. Towards 90% of addition, white precipitate formed suddenly. This mixture was stirred at −78° C. for 20 min, then, the dry ice bath was removed and the stirring was continued to allow the reaction mixture to warm to r.t. over 30 min. When the precipitate was dissolved, the reaction mixture was poured into ice-water (100 mL) and ether (50 mL). The two layers were separated; the aqueous layer was extracted with ether (3×50 mL). The combined organic layers were washed with brine, dried (K2CO3), filtered, and concentrated in vacuo to get 8.75 g (95% yield) of the title compound as a yellow liquid.

LCMS $R_T$=2.70 min.; MS 185 (M+H).

$^1$H NMR (300 MHz, CDCl3), δ (ppm): 5.55 (m, 1H), 5.02 (m, 2H), 3.85 (dt, 3.9 Hz, 12.0 Hz, 2H), 3.71 (s, 3H), 3.44 (dt, 2.4 Hz, 11.4 Hz, 2H), 2.30 (d, 7.5 Hz, 2H), 2.09 (m, 2H), 1.54 (m, 2H).

Intermediate (xxxvi)

4-(2-Oxo-ethyl)tetrahydro-pyran-4-carboxylic acid methyl ester

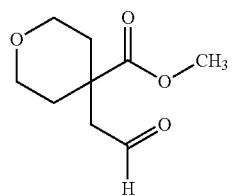

4-Allyl-tetrahydro-pyran-4-carboxylic acid methyl ester (11 g, 59.78 mmol) was dissolved in iPrOH (300 mL). To this was added a aqueous solution of NaIO$_4$ (28 g, 130.4 mmol, 2.18 equiv.) in water (300 mL), followed by addition of OsO$_4$ (50 mg, crystals, in one portion) at rt. The solution was stirred with a mechanical stirrer at rt (water bath). After 30 min, milky cloudy product was formed. Stirring was continued for 4 h. TLC (1% MeOH in DCM, and 5% MeOH in DCM) did not detect the SM. An aliquot was taken and dissolved in CDCl$_3$ to run NMR, there was no alkene peak in the sample. The reaction was judged to be complete. The reaction mixture was poured into ice water (200 mL) and EtOAc (200 mL). The two layers were separated and the aqueous layer was extracted with EtOAc (5×50 mL). More water was added to dissolve the solid resulting in a clear solution. The combined extracts were washed with brine, and concentrated to dryness to get a liquid. The liquid was subject to a reduced pressure distillation to remove isopropanol. The remaining liquid was purified on a 80-g silica gel column, eluted with MeOH in DCM: 0% 0-5 min; 5-10% 5-25 min. 10-12% 25-60 min. Note: the product is not UV active. Anisaldehyde visualization was used. The product fractions were collected and concentrated to yield a liquid 6.6 g (60% yield) of the title compound.

LCMS: R$_T$=1.26 min.; MS: 187(M+H).

$^1$H NMR (300 MHz, CDCl$_3$), δ (ppm): 9.68 (s, 1H), 3.85 (dt, 3.9 Hz, 12.0 Hz, 2H), 3.71 (s, 3H), 3.44 (dt, 2.4 Hz, 11.4 Hz, 2H), 2.30 (d, 7.5 Hz, 2H), 2.09 (m 2H), 1.54 (m, 2H).

Intermediate (xxxvii)

4-[2-(4-Bromo-2-methyl-phenylamino)-ethyl]-tetrahydro-pyran-4-carboxylic acid methyl ester

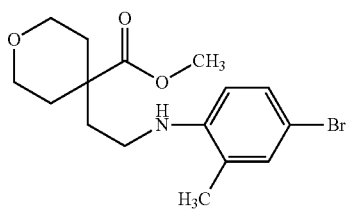

2-Methyl-4-bromo-aniline (1.20 g, 6.45 mmol) was dissolved in DCE (30 mL); to this solution was transferred a solution of 4-(2-Oxo-ethyl)-tetrahydro-pyran-4-carboxylic acid methyl ester (1.20 g, 6.44 mmol in DCE (30 mL). The flask was submerged in a water bath at rt. To this clear solution was then added acetic acid (1.2 g, 20 mmol, 3.1 equiv), followed by addition of powder NaBH(OAc)$_3$ (24.1 g, 19.3 mmol, 3 equiv. in 2 portions under N2 at r.t. The yellowish milky suspension was stirred at r.t. overnight. LC/MS showed m/z 356/358 at t=3.955 min. along with small amount of aniline sm at 2.078 (186/188). There was no di-alkylated product detected (MW 526.47). TLC (5% of MeOH in DCM) showed no SM aldehyde, but aniline. The reaction was diluted with DCM (30 mL), cooled to ice-water bath, and quenched with an aqueous solution of 10 mL of conc. NH$_4$OH (7.45M) in 30 mL of water. (2 M of NH$_4$OH). The two layers were separated, and the aqueous layer was extracted with DCM (20 mL×2). The combined DCM extracts were washed with sodium bicarbonate (20 mL), and brine (20 mL), dried (anhydrous potassium carbonate), filtered, and concentrated. The product was purified on a 40-g silica gel column (0-5% B: 0-4 min; 5-15% B 4-13 min; 20% B: 13-25 min (B is 10% MeOH in DCM) to get 2.00 g (87%) of the title compound as an oil.

LCMS: R$_T$=3.29 min.; MS: 356 (M+H).

$^1$H NMR (300 MHz, CDCl3), δ (ppm): 7.20 (dd, 2.3 Hz, 8.4 Hz, 1H), 7.14 (m, 1H), 6.42 (d, 8.4 Hz, 1H), 3.86 (dt, 3.6 Hz, 11.7 Hz, 2H), 3.69 (s, 3H), 3.51 (dt, 2.4 Hz, 11.4 Hz, 3H), 3.12 (m, 2H), 2.17 (m, 1H), 2.07 (s, 3H), 1.91 (t, 7.5 Hz, 3H), 1.58 (m, 2H).

Intermediate (xxxviii)

4-[2-(4-Bromo-2-fluoro-phenylamino)-ethyl]-tetrahydro-pyran-4-carboxylic acid methyl ester

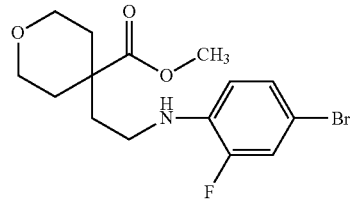

This intermediate is synthesized essentially in the same way as described above from 850 g of the aldehyde to obtain 1.4 g (85% yield) of the title product as tan oil.

LCMS: R$_T$=1.05 min.; MS: 360 (M+H)

Intermediate (xxxix)

4-[2-(4-Bromo-phenylamino)-ethyl]-tetrahydro-pyran-4-carboxylic acid methyl ester

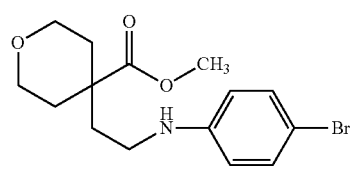

This intermediate is synthesized in the same way as described above from 850 g of the aldehyde to get 1.32 g (85% yield) of the title product as tan oil.

LCMS: R$_T$=1.0 min.; MS: 342 (M+H)

Intermediate (xxxx)

4-[2-(4-Bromo-2-trifluoromethyl-phenylamino)-ethyl]-tetrahydro-pyran-4-carboxylic acid methyl ester

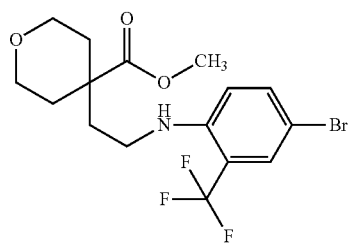

This intermediate is synthesized in the same way as described above from 850 g of the aldehyde to get 1.66 g (89% yield) of the title product as brown oil.

LCMS: $R_T$=1.12 min.; MS: 410 (M+H)

Intermediate (xxxxi)

4-[2-(4-Bromo-2-ethyl-phenylamino)-ethyl]-tetrahydro-pyran-4-carboxylic acid methyl ester

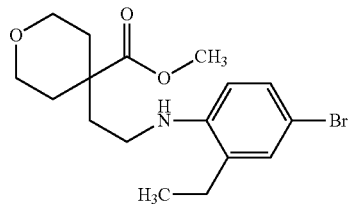

This intermediate is synthesized in the same way as described above from 850 g of the aldehyde to get 1.39 g (82% yield) of the title product as brown oil.

LCMS: $R_T$=1.10 min.; MS: 370 (M+H)

Intermediate (xxxxii)

2-(4-Bromo-2-methyl-phenyl)-8-oxa-2-aza-spiro[4.5]decan-1-one

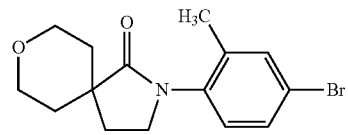

To a clear solution of 4-[2-(4-Bromo-2-methyl-phenylamino)-ethyl]-tetrahydro-pyran-4-carboxylic acid methyl ester (2 g, 5.6 mmol) in THF (80 mL) was added a solution of potassium t-butoxide (1M in THF) 2.5 mL (2.5 mmol, 0.45 equiv.) at r.t. (water bath at rt). The clear solution turned a little bit cloudy. After 30 min, TLC (5% MeOH in DCM) showed the reaction is complete (spot to spot), LC/MS detected the product peak of 324/326 (t 3.267 min). The reaction was cooled tin an ice-water bath, diluted with 100 mL of DCM, quenched with 20 mL of water. The two layers were separated. The aqueous layer was extracted with DCM (2×20 mL). The combined DCM extracts were washed with brine, and concentrated on rotavap to yield 1.79 g (98% yield) of the title product as a white solid.

LCMS: $R_T$=3.27 min.; MS: 324 (M+H).

$^1$H NMR (300 MHz, CDCl3), δ (ppm): 7.42 (d, 2.1 Hz, 1H), 7.36 (dd, 2.1 Hz, 8.4 Hz, 1H), 7.00 (d, 8.4 Hz, 1H), 4.06 (dt, 4.2 Hz, 11.7 Hz, 2H), 3.61 (m, 4H), 2.21 (t, 6.9 Hz, 2H), 2.17 (s, 3H), 2.11 (m, 2H), 1.51 (m, 2H).

Intermediate (xxxxiii)

2-(4-Bromo-2-fluoro-phenyl)-8-oxa-2-aza-spiro[4.5]decan-1-one

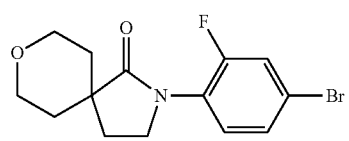

This intermediate is synthesized in the same way as described above from 1.40 g of the ester to get 590 mg (46% yield) of the title product as a tan solid.

LCMS: $R_T$=3.25 min.; MS: 328 (M+H).

$^1$H NMR (300 MHz, CDCl3) δ: 7.34 (3H, m), 4.03 (2H, dt, J=11.73, 4.22 Hz), 3.76 (2H, t, J=6.96 Hz), 3.60 (2H, m), 2.19 (2H, t, J=6.96 Hz), 2.08 (2H, m), 1.51 (2H, d, J=13.56 Hz).

Intermediate (xxxxiv)

2-(4-Bromo-phenyl)-8-oxa-2-aza-spiro[4.5]decan-1-one

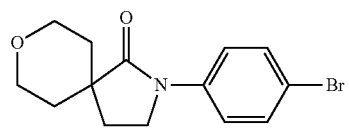

This intermediate is synthesized essentially in the same way as described above from 1.32 g of the ester to obtain 760 mg (63% yield) of the title product as a tan solid.

LCMS: $R_T$=3.42 min.; MS: 310 (M+H).

$^1$H NMR (300 MHz CDCl3) δ: 7.46 (2H, m), 7.57 (2H, m), 4.03 (2H, dt, J=11.73, 4.22 Hz), 3.78 (2H, t, J=6.78 Hz), 3.58 (2H, td, J=10.81, 2.57 Hz), 2.17 (2H, t, J=6.96 Hz), 2.08 (2H, m), 1.46 (2H, d, J=13.56 Hz).

Intermediate (xxxxv)

2-(4-Bromo-2-trifluoromethyl-phenyl)-8-oxa-2-aza-spiro[4.5]decan-1-one

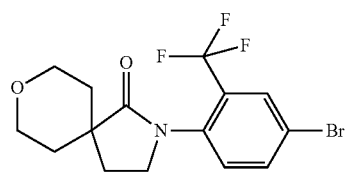

This intermediate is synthesized essentially in the same way as described above from 1.66 g of the ester to obtain 840 mg (55% yield) of the title product as a tan solid.

LCMS: $R_T$=3.45 min.; MS: 378 (M+H).

¹H NMR (300 MHz CDCl3) δ: 7.87 (1H, d, J=2.20 Hz), 7.74 (1H, dd, J=8.43, 1.83 Hz) 7.15 (1H, d, J=8.43 Hz), 4.03 (2H, dt, J=11.73, 4.40 Hz), 3.63 (4H, m), 2.22 (2H, t, J=6.96 Hz), 2.08 (2H, m), 1.51 (2H, d, J=13.75 Hz).

Intermediate (xxxxvi)

2-(4-Bromo-2-ethyl-phenyl)-8-oxa-2-aza-spiro[4.5]decan-1-one

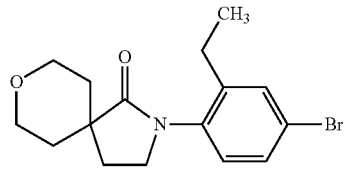

Intermediate (xxxxvii)

This intermediate is synthesized essentially in the same way as described above from 1.39 g of the ester to obtain 560 mg (55% yield) of the title product as a tan solid.
MS: 338.08 (M+H).
¹H NMR (300 MHz, CDCl3) δ: 7.45 (1H, d, J=2.20 Hz), 7.35 (1H, dd, J=8.43, 2.20 Hz), 6.97 (1H, d, J=8.43 Hz), 4.04 (2H, dt, J=11.73, 4.22 Hz), 3.62 (4H, m), 2.51 (2H, q, J=7.51 Hz), 2.21 (2H, t, J=6.96 Hz), 1.49 (2H, d, 13.38 Hz), 1.20 (3H, t, J=7.51 Hz).

Intermediate (xxxxviii)

4-But-3-enyl-tetrahydro-pyran-4-carboxylic acid methyl ester

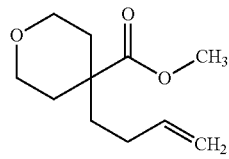

In a 250-mL round bottom flask was weighed 6.1 g (60 mmol) of diisopropylamine and dissolved in THF. This solution was cooled to −78° C. To this was added 24 mL of 2 M butyllithium in hexane and stirred for 15 min, warmed up to 0° C. for 20 min, re-cooled to −78° C. To this was added tetrahydro-pyran-4-carboxylic acid methyl ester (7.2 g, 50 mmol) in THF (10 mL). There was almost no color change (light a little bit). This was stirred at −78° C. for 45 min. Then, a mixture of 5 g of HMPA and bromo-butene (8.78 g, 65 mmol) was added via cannula at −78° C. There was no noticeable change. About half was added, the ice-acetone bath was removed. When addition was complete, the flask was submerged into an ice-water bath, stirred for 20 min; then, rt for 2 h. TLC (EtOAc/Heptane 1:1, paraldehyde visualization) showed the reaction was complete. The reaction mixture was poured into ice-water (100 mL) and ether (50 mL). The two layers were separated; the aqueous layer was extracted with ether (3×50 mL). The combined organic layers were washed with brine, dried (K₂CO₃), filtered, and concentrated in vacuo to obtain 10.4 g (87%) of the title product as a slightly yellow liquid. The material is pure enough to be used in the next step reaction without further purification.

LCMS: $R_T$=3.07 min.; MS: 199 (M+H).
NMR (CDCl3, 300 MHz) δ: 5.78 (ddt, 8.4 Hz, 11.7 Hz, 6.6 Hz, 1H), 4.97 (m, 2H), 3.90 (dt, 3.9 Hz, 11.7 Hz, 2H), 3.72 (s, 3H), 3.41 (dt, 2.6 Hz, 11.7 Hz, 2H), 2.10 (m, 2H), 1.98 (m, 2H), 1.58 (m, 4H).

Intermediate (xxxxix)

4-(3-Oxo-propyl)-tetrahydro-pyran-4-carboxylic acid methyl ester

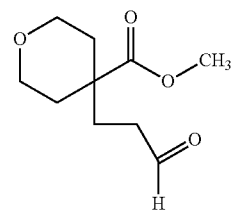

4-But-3-enyl-tetrahydro-pyran-4-carboxylic acid methyl ester (6 g, 30 mmol) was dissolved in iPrOH (150 mL). To this was added a aqueous solution of NaIO4 (14 g, 65.2 mmol, 2.18 equiv.) in water (150 mL), followed by addition of OsO₄ (25 mg, crystals, in one portion) at rt. The solution was stirred with a mechanical stirrer at rt (water bath). After 30 min, milky cloudy product was formed. Stirring was continued for 4 h. TLC (1% MeOH in DCM, and 5% MeOH in DCM) did not detect the SM. An aliquot was taken and dissolved in CDCl₃ to run NMR, there was no alkene peak in the sample. The reaction was judged to be complete. The reaction mixture was poured into ice water (200 mL) and EtOAc (200 mL). The two layers were separated and the aqueous layer was extracted with EtOAc (5×50 mL). More water was added to dissolve the solid resulting in a clear solution. The combined extracts were washed with brine, and concentrated to dryness to get a liquid. The liquid was subject a reduced distillation to remove isopropanol. The remaining liquid was purified on a 50-g silica gel column, eluted with 50% EtOAc in Heptane. Note: the product is not UV active. Anisaldehyde visualization was used. The product fractions were collected and concentrated to yield 5.62 g (94% yield) of the title compound as a liquid.

LCMS: $R_T$=2.10 min.; MS: 201 (M+H).
¹H NMR (CDCl3, 300 MHz) δ: 9.74 m, 1H), 3.86 (dt, 3.6 Hz, 11.7 Hz, 2H), 3.72 (s, 3H), 3.41 (dt, 2.3 Hz, 11.7 Hz, 2H), 2.42 (m, 2H), 2.09 (m, 2H), 1.88 (m, 2H), 1.52 (m, 2H).

Intermediate (D)

4-[3-(4-Bromo-2-methyl-phenylamino)-propyl]-tetrahydro-pyran-4-carboxylic acid methyl ester

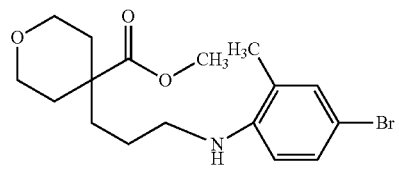

2-Methyl-4-bromo-aniline (930 mg, 5 mmol) was dissolved in DCE (50 mL); to this solution was transferred a solution of 4-(3-oxo-propyl)-tetrahydro-pyran-4-carboxylic acid methyl ester (1.0 g, 5 mmol) in DCE (50 mL). The flask was submerged in a water bath at rt. To this clear solution was then added acetic acid (930 mg, 15.5 mmol, 3.1 equiv), followed by addition of powder NaBH(OAc)₃ (3.18 g, 15 mmol, 3 equiv.) in 1 portion under N2 at r.t. The yellowish milky suspension was stirred at r.t. overnight. LC/MS showed m/z 372/370 at t=3.872 min. along with small amount of aniline starting material (MS: 186/188). TLC (5% of MeOH in DCM) showed no SM. of aldehyde, but aniline. The reaction was diluted with DCM (100 mL), cooled to ice-water bath, and quenched with 5 mL of conc. NH₄OH (7.45M) in 150 mL of water. (2 M of NH4OH). The two layers were separated, and the aqueous layer was extracted with DCM (20 mL×2). The combined DCM extracts were washed with sodium bicarbonate (10 mL), and brine (10 mL), dried (anhydrous potassium carbonate), filtered, and concentrated. The product was purified on a 25-g-silica gel column eluted with DCM to elute aniline; 2.5% MeOH in DCM for the product to get 0.85 g (46%) of the title compound as an oil.

LCMS: $R_T$=3.872 min.; MS: 372/370 (M+H).

Intermediate (Di)

4-[3-(4-Bromo-phenylamino)-propyl]-tetrahydro-pyran-4-carboxylic acid methyl ester

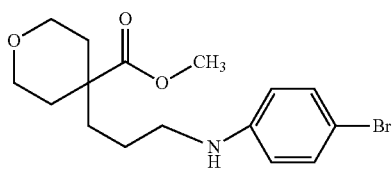

This intermediate was synthesized essentially in the same way as above to obtain 0.74 g (42% yield) of the title compound as an oil.

LCMS: $R_T$=3.382 min.; MS: 356/358 (M+H).

Intermediate (iii)

4-[3-(4-Bromo-2-fluoro-phenylamino)-propyl]-tetrahydro-pyran-4-carboxylic acid methyl ester

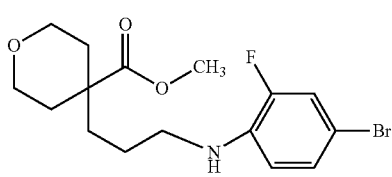

This intermediate was synthesized essentially in the same way as above to obtain 0.62 g (33% yield) of the title compound as an oil.

LCMS: $R_T$=4.253 min.; MS: 374/376 (M+H).

Intermediate (viii)

2-(4-Bromo-2-methyl-phenyl)-9-oxa-2-aza-spiro[5.5]undecan-1-one

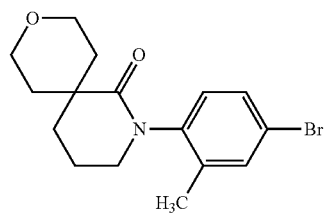

To a clear solution of 4-[3-(4-bromo-2-methyl-phenylamino)-propyl]-tetrahydro-pyran-4-carboxylic acid methyl ester (0.85 g, 2.3 mmol) in THF (25 mL) was added NaH (60% in mineral oil, ~100 mg) and the reaction temperature was raised to 50° C. (external) for 2 h. TLC (2.5% MeOH in DCM for SM, 5% MeOH in DCM for product) showed the reaction was complete. LC/MS detected the product peak. The reaction was cooled tin an ice-water bath, diluted with 25 mL of ethyl acetate, quenched with 10 mL of water. The two layers were separated. The aqueous layer was extracted with EtOAc (2×10 mL). The combined EtOAc extracts were washed with brine, and concentrated on rotavap to yield a crude product as a slightly yellow solid. This material was loaded onto a 25-g of silica gel column, eluted with DCM and 5% MeOH in DCM to get 0.81 g (95% yield) of the title compound as a white solid.

LCMS: $R_T$=3.03 min.; MS: 338/340 (M+H).
¹H NMR (CDCl₃, 300 MHz) δ (ppm): 7.35 (m, 2H), 6.96 (m, 1H), 3.96 (m, 2H), 3.75-3.52 (m, 2H), 3.37 (m, 2H), 2.22 (m, 2H), 2.12 (s, 3H), 1.98-2.10 (m, 4H), 1.53 (m, 2H).

Intermediate (Div)

2-(4-Bromo-phenyl)-9-oxa-2-aza-spiro[5.5]undecan-1-one

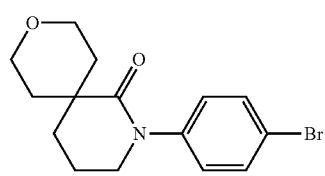

To a clear solution of 4-[3-(4-Bromo-phenylamino)-propyl]-tetrahydro-pyran-4-carboxylic acid methyl ester (0.74 g, 2.08 mmol) in THF (25 mL) was added a solution of 1.0 mL of potassium t-butoxide (1M in THF) at r.t. (water bath at rt). The clear solution turned a little bit cloudy. After 15 min, TLC (5% MeOH in DCM) showed the reaction is complete (spot to spot), LC/MS detected the product peak. The reaction was cooled tin an ice-water bath, diluted with 25 mL of ethyl acetate, quenched with 10 mL of water. The two layers were separated. The aqueous layer was extracted with EtOAc (2×10 mL). The combined EtOAc extracts were washed with brine, and concentrated on rotavap to yield a crude product as a slightly yellow solid. This material was loaded onto a 25-g of silica gel column, eluted with DCM and 5% MeOH in DCM to get 0.64 g (86% yield) of the title compound as a white solid.

LCMS: $R_T$=2.91 min.; MS: 324/326 (M+H).

$^1$H NMR (CDCl3, 300 MHz) δ (ppm): 7.50 (d, 9.3 Hz, 2H), 7.11 (d, 9.3 Hz, 2H), 3.95 (m, 2H), 3.73-3.61 (m, 2H), 2.12 (m, 2H), 1.98 (bs, 4H), 1.52 (m, 2H).

Intermediate (Dv)

2-(4-Bromo-2-fluoro-phenyl)-9-oxa-2-aza-spiro[5.5]undecan-1-one

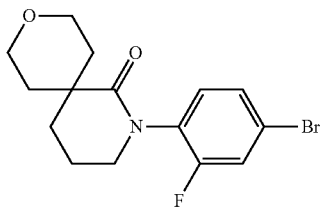

This intermediate was synthesized substantially the same way as above to obtain 0.53 g (85% yield) of the title compound as a white solid.

LCMS: $R_T$=3.01 min.; MS:342/344 (M+H).

$^1$H NMR (CDCl3, 300 MHz) δ (ppm): 7.31 (m, 2H), 7.10 (m, 1H), 3.94 (bs, 2H), 3.70 (m, 2H), 3.56 (bs, 2H), 2.22 (bs, 2H), 1.99 (m, 4H), 1.56 (m, 3H).

Example 1

2-[2-Methyl-4-((2S,3'S)-2-methyl-[1,3']bipyrrolidinyl-1'-yl)-phenyl]-8-oxa-2-aza-spiro[4.5]decan-1-one

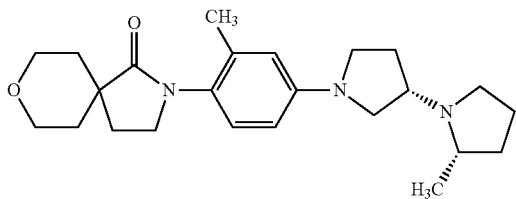

Method A: Step 1

4-{2-[2-Methyl-4-((2S,3'S)-2-methyl-[1,3']bipyrrolidinyl-1'-yl)-phenylamino]-ethyl}-tetrahydro-pyran-4-carboxylic acid methyl ester

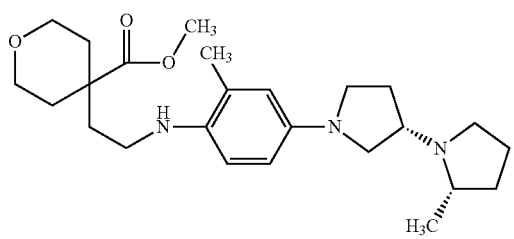

2-Methyl-4-((2S,3'S)-2-methyl-[1,3']bipyrrolidinyl-1'-yl)-phenylamine (4.56 mmol) was dissolved in DCE (20 mL); to this solution was transferred a solution of 4-(2-Oxo-ethyl)-tetrahydro-pyran-4-carboxylic acid methyl ester (0.85 g, 4.56 mmol) in DCE (50 mL). To this clear solution was then added acetic acid (0.86 g, 14.3 mmol, 3.1 equiv), followed by addition of powder NaBH(OAc)$_3$ (CSN: 56553-60-7, mw=211.94): 2.9 g, 13.6 mmol, 3 equiv.) in one portion under N$_2$ at r.t. The yellowish milky solution was stirred at r.t. overnight. LC/MS showed m/z 429.35/430.40 at t=2.123 min. TLC (5% of 7N NH$_3$/MeOH in DCM) showed no SM. The reaction was diluted with DCM (40 mL) and quenched with 30 mL of conc. NH$_4$OH in 70 mL of water. The two layers were separated, and the aqueous layer was extracted with DCM (10 mL×2). The combined DCM extracts were washed with sodium bicarbonate (10 mL), and brine (15 mL), dried (anhydrous potassium carbonate), filtered, and concentrated. The product was purified on a 25 g-silica gel column (0-20%, 0-4 min; 20-40: 4-13 min; 40%: 13-25 min (A is % of 7N NH3/MeOH in DCM) to get 1.17 g (60%) of the title compound as an oil.

LC $R_T$=2.72 min.; MS 430

$^1$H NMR (300 MHz, CDCl$_3$), δ (ppm): 6.56 (d, 9.3 Hz, 1H), 6.41 (m, 2H), 3.83 (m, 2H), 3.71 (s, 3H), 3.53-3.41 (m, 3H), 3.35-2.88 (m, 8H), 2.76 (sixtet, 6.0 Hz, 1H), 2.50 (q, Step 2

To a clear solution of 4-{2-[2-Methyl-4-((2S,3'S)-2-methyl-[1,3']bipyrrolidinyl-1'-yl)-phenylamino]-ethyl}-tetrahydro-pyran-4-carboxylic acid methyl ester (0.79 g, 1.84 mmol) in THF (70 mL) was added a solution of potassium t-butoxide (1M in THF) 1 mL (2 mL, 2 mmol, 1.1 equiv.) at r.t. The clear solution turned a little bit cloudy. After 15 min, TLC (5% of 7N NH$_3$/MeOH in DCM) showed the reaction is complete (spot to spot), LC/MS detected the product peak of 398 (t=2.491 min) with trace of starting material peak of 430/429. The stirring was continued for 45 min more and the reaction is complete by LC/MS. The reaction mixtures were quenched by dilution with DCM (20 mL) and water (10 mL) and sodium bicarbonate (5 mL). The two layers were separated. The aqueous layer was extracted with DCM (2×10 mL). The combined DCM extracts were washed with brine, dried (K$_2$CO$_3$), filtered, and concentrated on rotavap to yield a crude product, almost pure. This material was dissolved in DCM (1 mL), loaded onto a 25-g of silica gel column, eluted with A in DCM: 0-40%, 0-4 min; 40-50 4-13 min; 50-70 13-25 min (A is % of 7N NH$_3$/MeOH in DCM) to get 0.92 g (85%) of the pure compound 10. LC/MS 100% pure, MS 398.

Method B (2S,3'S)-2-Methyl-[1,3']bipyrrolidinyl dihydrochloride (2HCl.2H$_2$O, MW 263.18) (5.97 g, 22.71 mmol, 1.11 equiv.) was dissolved in 10 mL of MeOH with the aid of sonication. To the solution was added 100 mL of DCM. The solution was cooled to an ice-water bath. To this solution was added powder KOH (3.9 g, 59.02 mmol, 2.6 equiv. to the amine salt) with stirring under N$_2$. The stirring was continued for 1 h. 2 g of powder K$_2$CO$_3$ was added with stirring to form a nice suspension. The suspension was filtered through a Celite pad, rinsed with DCM until no amine was leach out by TLC (20% MeOH in DCM, anisaldehyde visualization, white spot just above the origin). The solution was concentrated to dryness; the residue was further dried under high vacuum with stirring for 1 h, re-dissolved in 50 mL of anhydrous toluene and ready to use.

An 250-mL RBF containing a stir bar was charged with Pd$_2$(dba)$_3$ (186 mg, 0.2036 mmol, 0.01 equiv.), 2-dicyclohexylphosphino-2',4',6'-triisopropylbiphenyl 1 (485 mg, 1.018 mmol, 0.05 equiv.), 2-(4-Bromo-2-methyl-phenyl)-8-oxa-2-aza-spiro[4.5]decan-1-one (6.6 g, 20.36 mmol, 1 equiv.), and sodium t-butoxide (4.891 g, 50.9 mmol, 2.5 equiv.). The flask was de-gassed and refilled with $N_2$ three cycles. 100 mL of anhydrous toluene was introduced and the red solution was stirred for 2 min at rt, then the amine (22.71 mmol, 1.11 equiv., obtained from above) in toluene was introduced into the flask via cannula. The flask was evacuated and backfilled with $N_2$. The reaction was heated in an oil bath set at 90° C. for 2.5 h, allowed to cool down to room temperature and quenched with water (20 mL). The mixture was extracted with DCM (3×100 mL). The combined DCM extracts were washed with sodium bicarbonate (50 mL), and brine (50 mL), dried (anhydrous potassium carbonate), filtered, and concentrated. The crude product was purified on a 80-g silica gel column on Analogix. Gradient: B %/time: 0/0-10 min; 0-50%/10-15 min; 50-90%/15-60 min (A=DCM; B=5% of 7N NH3 in MeOH in DCM) to get 6.6 g (82%) of the title compound as a gummy semi-solid. The material was re-crystallized from MTBE and DCM to get a colorless crystalline solid.

Mp. 135.5° C.

Elemental analysis: C 72.51% H 8.87% N 10.57%

Found: C 72.51%, H 9.07%, N 10.65%

LCMS $R_T$=1.96 min.; MS: 398 (M+H).

$^1$H NMR (300 MHz, CDCl3), δ (ppm): 6.94 (m, 1H), 6.39 (m, 2H), 4.05 (dt, 4.2 Hz, 11.7 Hz, 2H), 3.64-3.47 (m, 10H), 3.37 (dt, 2.6 Hz, 9.0 Hz, 1H), 2.76 (sixtet, 6.3 Hz, 1H), 2.52 (q, 8.4 Hz, 1H), 2.14 (s, 3H), 2.12 (m, 4H), 1.98 (m, 2H), 1.77 (m, 2H), 1.48 (m, 3H), 1.14 (d, 6.3 Hz, 3H).

Optical rotation: [α]D=+27.2° (c 0.5, MeOH)

Chiral purity: 99.9% (Chiral HPLC).

The product from Method A and Method B exactly match each other in NMR, LCMS, and Rotation.

Example 2

2-[2-Methyl-4-((2S,3'S)-2-methyl-[1,3']bipyrrolidinyl-1'-yl)-phenyl]-9-oxa-2-aza-spiro[5.5]undecan-1-one

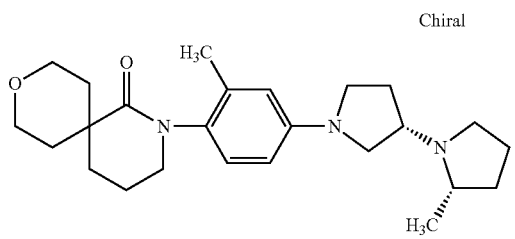

The title compound was synthesized from Method A.

LCMS: $R_T$=1.98 min.; MS: 412 (M+H).

$^1$H NMR (300 MHz, CDCl3), δ (ppm): 6.93 (d, 9.3 Hz, 1H), 6.39 (m, 2H), 3.98 (m, 2H), 3.75-3.14 (m, 9H), 3.01 (m, 1H), 2.76 (m, 1H), 2.53 (q, 8.4 Hz, 1H), 2.31-2.10 (m, 4H), 2.10 (s, 3H), 1.96 (m, 5H), 1.76 (m, 2H), 1.50 (m, 3H), 1.13 (d, 6.3 Hz, 3H).

Example 3

2-[4-((2S,3'S)-2-Methyl-[1,3']bipyrrolidinyl-1'-yl)-phenyl]-8-oxa-2-aza-spiro[4.5]decan-1-one

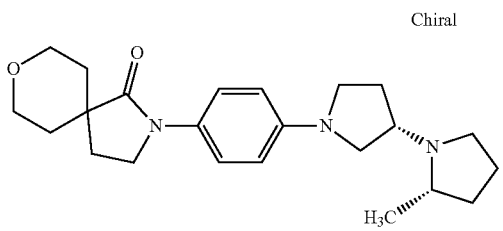

This compound was synthesized by the Method A.

LCMS: $R_T$=1.9 min.; MS: 384 (M+H).

$^1$H NMR (300 MHz, CDCl3), δ (ppm): 7.45 (d, 2H), 6.57 (d, 2H), 4.04-3.98 (m, 2H), 3.77-3.71 (m, 4H), 3.61-3.53 (m, 4H), 3.49-3.39 (m, 2H), 3.30-3.24 (m, 2H), 2.97-2.93 (m, 1H), 2.30-2.25 (m, 2H), 2.18-2.02 (m, 8H), 1.82-1.70 (m, 1H), 1.40 (d, 3H).

Example 4

2-[3-Fluoro-4-((2S,3'S)-2-methyl-[1,3']bipyrrolidinyl-1'-yl)-phenyl]-8-oxa-2-aza-spiro[4.5]decan-1-one

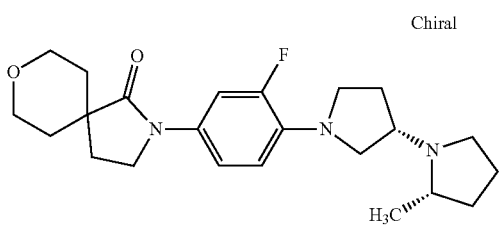

The title compound was synthesized following substantially the procedures as set forth in Method A, Example 1 and employing the corresponding starting materials.

LCMS: $R_T$=2.36 min.; MS: 402 (M+H).

$^1$H NMR (300 MHz, CDCl3), δ (ppm): 7.54 (dd, 1H), 7.15 (dd, 1H), 6.68 (t, 1H), 4.05-3.99 (m, 2H), 3.85-3.71 (m, 4H), 3.65-3.45 (m, 6H), 3.42-3.33 (m, 2H), 2.92 (q, 1H), 2.23-1.99 (m, 10H), 1.80-1.71 (m, 1H), 1.36 (d, 3H).

Example 5

2-{2-Methyl-4-[4-((S)-2-methyl-pyrrolidin-1-yl)-piperidin-1-yl]-phenyl}-8-oxa-2-aza-spiro[4.5]decan-1-one Step 1: 2-[4-(4-Hydroxy-piperidin-1-yl)-2-methyl-phenyl]-8-oxa-2-aza-spiro[4.5]decan-1-one

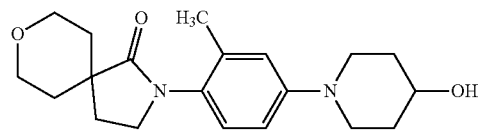

An 25-mL round bottom flask containing a stir bar was charged with $Pd_2(dba)_3$ (00.01 equiv., 0.0154 mmol, 14 mg.), 2-dicyclohexylphosphino-2',4',6'-triisopropylbiphenyl (0.05 equiv., 0.077 mmol, 36.7 mg), 2-(4-bromo-2-methylphenyl)-8-oxa-aza-spiro[4.5]decan-1-one (0.50 g, 1.54 mmol, 1 equiv.), and sodium t-butoxide (2.5 equiv., 3.85 mmol, 370 mg.), and piperidin-4-ol (1.5 equiv., 2.3 mmol, 234 mg). The vial was capped with a rubber septum, evacuated and backfilled with N₂. To this vial was introduced 8 mL of anhydrous toluene. The reaction was heated in an oil bath set at 90° C. for 2 h, allowed to cool down to room temperature and quenched with water (2 mL). The two layers were separated and the aqueous layer was extracted with DCM (3×10 mL). The combined DCM extracts were washed with sodium bicarbonate (50 mL), and brine (50 mL), dried (anhydrous potassium carbonate), filtered, and concentrated. The crude product was purified by a silica gel column to give 75.1 mg (14% yield) of the title compound as a light yellow solid after standing.

LCMS: R$_T$=1.42 min.; MS: 345 (M+H)

¹H NMR (300 MHz, CDCl3), δ (ppm): 6.99 (d, 8.4 Hz, 1H), 6.78 (m, 2H), 4.05 (dt, 4.2 Hz, 11.7 Hz, 2H), 3.83 (m, 1H), 3.58 (m, 5H), 2.91 (m, 2H), 2.17 (m, 4H), 2.10 (s, 3H), 1.63 (m, 8H).

Step 2: 2-{2-Methyl-4-[4-((S)-2-methyl-pyrrolidin-1-yl)-piperidin-1-yl]-phenyl}-8-oxa-2-aza-spiro[4.5]decan-1-one

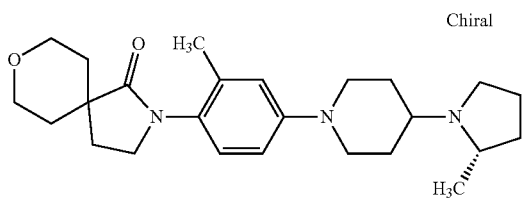

A round bottomed flask equipped with a stir bar and a septum was charged with p-toluenesulfonyl chloride (2 equiv., 0.47 mmol, 89 mg) and 5 ml of anhydrous DCM. To this solution was added a solution of 2-[4-(4-Hydroxy-piperidin-1-yl)-2-methyl-phenyl]-8-oxa-2-aza-spiro[4.5]decan-1-one (75 mg, 0.21 mmol.), followed by Et₃N and a few crystals of DMAP. The solution was stirred under nitrogen overnight from 0° C. to rt. TLC (5% MeOH in DCM for SM and DCM for product) showed the reaction was almost complete. The reaction was quenched by addition of polymer-supported amine (3.2 mmol/g, 150 mg), stirred 30 min. The suspension was filtered, rinsed with DCM. The filtrate was concentrated to dryness and further dried under high vacuum for 1 h to get an intermediate tosylate (MW=498.65), LCMS gave 499.

The tosylate obtained above was dissolved in 3 mL of anhydrous CH₃CN. To this solution was added 64 mg of (S)-(+)-2-methyl pyrrolidine and 120 mg of K₂CO₃ powder anhydrous. The suspension was heated over an oil bath set at 80° C. for overnight. Acetonitrile was evaporated. The residue was dissolved in DCM (10 mL) and water (5 mL). The two layers were separated and the aqueous layer was extracted with DCM (2×4 mL). The combined DCM extracts was extracted with 1N HCl (2×5 mL). The aqueous solution was cooled in an ice-water bath and 10 mL of DCM was added. The mixture was basified to pH 8 and the two layers were separated and the aqueous layer was extracted with DCM (2×4 mM). The combined DCM extracts was washed with brine (5 mL), dried (K₂CO₃), filtered, and concentrated to a residue. This was purified on a silica gel column eluted with 5% of 7N NH3/MeOH in DCM to get 70 mg (80% yield) of the title compound as a white solid.

LCMS: R$_T$=2.24 min.; MS: 412 (M+H)

¹H NMR (300 MHz, CDCl3), δ (ppm): 6.98 (d, 8.4 Hz, 1H), 6.77 (m, 2H), 4.05 (dt, 4.2 Hz, 11.7 Hz, 2H), 3.76-3.53 (m, 5H), 2.97-2.51 (m, 4H), 2.15 (m, 2H), 2.14 (s, 3H), 1.96-1.42 9M, 15H), 1.08 (d, 6.3 Hz, 3H).

Example 6

2-[2-Methyl-4-((2R,3'S)-2-methyl-[1,3']bipyrrolidinyl-1'-yl)-phenyl]-8-oxa-2-aza-spiro[4.5]decan-1-one

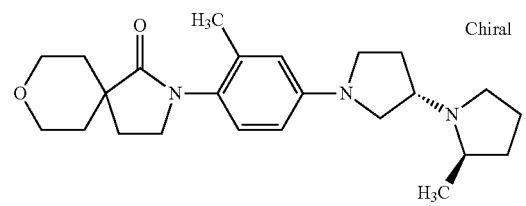

The title compound was synthesized in substantially the same way as Example 1, Method B, in 46% yield.

LC R$_T$=1.95 min.; MS 398.

¹H NMR (300 MHz, CDCl3), δ: 6.96 (m, 1H), 6.39 (m, 2H), 4.05 (dt, 4.2 Hz, 11.4 Hz, 2H), 3.64-3.47 (m, 10H), 3.37 (dt, 3.6 Hz, 9.0 Hz, 1H), 2.79 (sixtet, 6.3 Hz, 1H), 2.56 (q, 8.4 Hz, 1H), 2.17 (m, 4H), 2.14 (s, 3H), 1.98-1.69 (m, 4H), 1.48 (m, 3H), 1.14 (d, 6.3 Hz, 3H).

Example 7

2-[4-(2-Ethyl-[1,3']bipyrrolidinyl-1'-yl)-2-fluoro-phenyl]-8-oxa-2-aza-spiro[4.5]decan-1-one

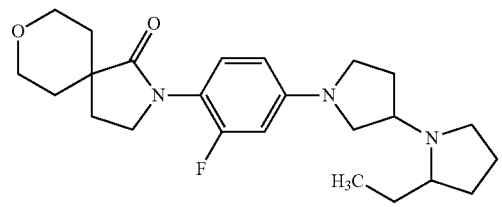

The title compound is synthesized by the Method B, from 60 mg of the bromide to get 22.6 mg (30% yield) of the product a brown gum.

LC R$_T$=2.11 min.; MS 416.

¹H NMR (300 MHz CDCl₃) δ 7.12 (1H, t, J=9.35 Hz), 6.27 (2H, m), 4.03 (2H, dt, J=11.73, 4.22 Hz), 3.66 (2H, t, J=Hz), 3.59 (2H, m), 3.49-3.16 (5H, m), 3.01 (1H, m), 2.54 (2H, m), 2.20-2.03 (7H, m), 1.83-1.61 (3H, m), 1.49 (3H, d, J=13.75 Hz), 1.27 (1H, m), 0.90 (3H, td, J=7.33, 1.83 Hz).

Example 8

2-[2-Fluoro-4-(2-isopropyl-[1,3']bipyrrolidinyl-1'-yl)-phenyl]-8-oxa-2-aza-spiro[4.5]decan-1-one

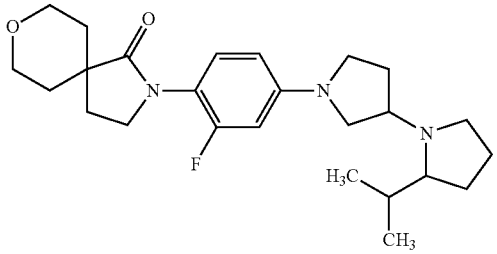

The title compound is synthesized following substantially the same procedures as set forth in Method B, Example 1 starting from 60 mg of the bromide to obtain 64.1 mg (83% yield) of the product as a brown gum.

LC $R_T$=2.15 min.; MS 430.

$^1$H NMR (300 MHz CDCl$_3$) δ 7.13 (1H, m), 6.26 (2H, m), 4.04 (2H, dt, J=11.55, 3.67 Hz), 3.64 (4H, m), 3.38 (2H, m), 3.22 (2H, m), 3.00 (1H, m), 2.48 (2H, m), 2.13 (7H, m), 1.65 (4H, m), 1.50 (3H, m), 0.87 (6H, m).

Example 9

2-[2-Fluoro-4-(2-propyl-[1,3']bipyrrolidinyl-1'-yl)-phenyl]-8-oxa-2-aza-spiro[4.5]decan-1-one

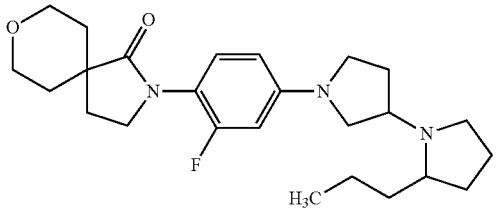

The title compound is synthesized following substantially the same procedures as set forth in Method B, Example 1 starting from 60 mg of the bromide to obtain 35 mg (45% yield) of the product a brown gum.

LC $R_T$=2.17 min.; MS 430.

$^1$H NMR (300 MHz CDCl$_3$) δ 7.12 (1H, t, J=9.16 Hz), 6.27 (2H. m), 4.03 (2H, dt, J=11.73, 4.22 Hz), 3.70-3.54 (4H, m), 3.50-3.18 (5H, m), 3.02 (1H, m), 2.65 (1H, m), 2.53 (1H, m), 2.11 (7H, m), 1.97-1.68 (2H, m), 1.52 (4H, m), 1.29 (3H, m), 0.94 (3H, m).

Example 10

2-{2-Fluoro-4-[4-((S)-2-methyl-pyrrolidin-1-yl)piperidin-1-yl]-phenyl}-8-oxa-2-aza-spiro[4.5]decan-1-one

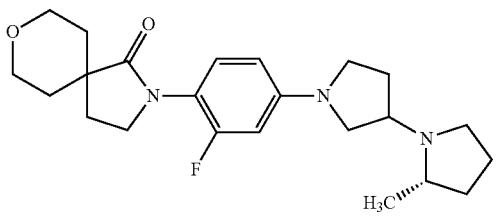

The title compound is synthesized following substantially the same procedures as set forth in Method B, Example 1 starting from 60 mg of the bromide to obtain 45.8 mg (61% yield) of the product a brown gum.

LC $R_T$=1.87 min.; MS 416.

$^1$H NMR (300 MHz CDCl$_3$) δ 7.18 (1H, t, J=8.98 Hz), 6.66 (2H, m), 4.04 (2H, m), 3.77-3.55 (6H, m), 2.91 (2H, m), 2.73 (2H. m), 2.58 (2H, m), 1.11 (4H, m), 2.01-1.57 (7H, m), 1.50 (3H, m), 1.07 (3H, d, J=6.23 Hz).

Example 11

2-[2-Fluoro-4-((2S,3'S)-2-methyl-[1,3']bipyrrolidinyl-1'-yl)-phenyl]-8-oxa-2-aza-spiro[4.5]decan-1-one

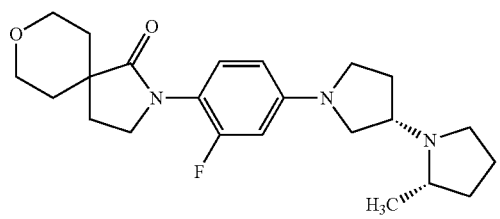

The title compound is synthesized following substantially the same procedures as set forth in Method B, Example 1 starting from 60 mg of the bromide to get 42.9 mg (59% yield) of the product a brown gum.

LC $R_T$=1.97 min.; MS 402.

$^1$H NMR (300 MHz CDCl$_3$) δ 7.11 (1H, t, 9.16 Hz), 6.27 (2H, m), 4.03 (2H, dt, J=11.73, 4.22 Hz), 3.62 (4H, m), 3.48 (1H, t, J=6.96 Hz), 3.42-3.17 (4H, m), 3.01 (1H, m), 2.79 (1H, m), 2.53 (1H, J=8.25 Hz), 2.25-1.91 (7H, m), 1.78 (2H, m), 1.49 (3H, d, J=13.75 Hz), 1.12 (3H, d, J=6.23 Hz).

Example 12

2-[2-Fluoro-4-((S)-2-methyl-[1,4']bipiperidinyl-1'-yl)-phenyl]-8-oxa-2-aza-spiro[4.5]decan-1-one

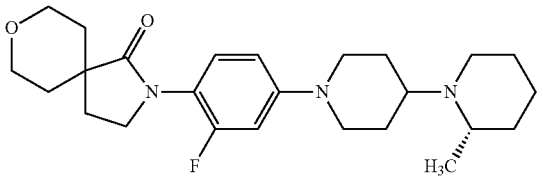

The title compound is synthesized following substantially the same procedures as set forth in Method B, Example 1 starting from 60 mg of the bromide to obtain 24.4 mg (32% yield) of the product as a brown gum.

LC $R_T$=2.03 min.; MS 430.

$^1$H NMR (300 MHz CDCl$_3$) δ 7.19 (1H, t, J=9.16 Hz), 6.65 (2H, m), 4.03 (2H, dt, J=11.73, 4.22 Hz), 3.76 (1H, m), 3.69 (1H, t, J=6.96 Hz), 3.59 (2H, m), 3.42-2.93 (2H, m), 2.77 (4H, m), 2.38 (2H, m), 2.22-2.01 (7H, m), 1.97-1.60 (6H, m), 1.49 (3H, d, J=13.75), 1.26 (3H, m).

Example 13

2-{4-[4-(2-Isopropyl-pyrrolidin-1-yl)-piperidin-1-yl]-phenyl}-8-oxa-2-aza-spiro[4.5]decan-1-one

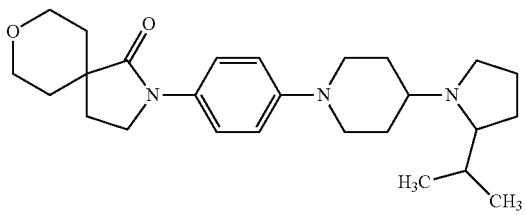

The title compound is synthesized following substantially the same procedures as set forth in Method B, Example 1 starting from 100 mg of the bromide to obtain 60 mg (44% yield) of the product as a brown gum.

LC $R_T$=2.08 min.; MS 426.

$^1$H NMR (300 MHz CDCl$_3$) δ 7.50 (2H, d, J=9.16 Hz), 6.93 (2H, d, J=9.16 Hz), 4.02 (2H, dt, J=11.55, 4.22 Hz), 3.76 (2H, t, J=6.78 Hz), 3.69 (2H, m), 3.57 (2H, td, J=11.00, 2.57 Hz), 2.92 (1H, m), 2.77-2.49 (5H, m), 2.17-2.01 (4H, m), 1.89-1.51 (9H, m), 1.44 (2H, d, J=13.56), 0.86 (6H, dd, J=16.13, 6.78 Hz).

Example 14

2-{4-[4-(2-Propyl-pyrrolidin-1-yl)-piperidin-1-yl]-phenyl}-8-oxa-2-aza-spiro[4.5]decan-1-one

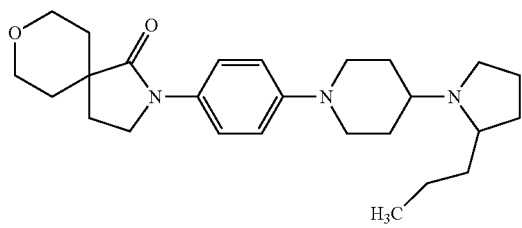

The title compound is synthesized following substantially the same procedures as set forth in Method B, Example 1 starting from 100 mg of the bromide to get 75.8 mg (56% yield) of the product as a brown gum.

LC $R_T$=2.16 min.; MS 426.

$^1$H NMR (300 MHz CDCl$_3$) δ: 7.50 (2H, d, J=8.98 Hz), 6.93 (2H, d, J=8.98 Hz), 4.02 (2H, dt, J=11.73, 4.03 Hz), 3.75 (2H, t, J=6.78 Hz), 3.70 (2H, d, J=12.28 Hz), 3.58 (2H, td, J=11.00, 2.57 Hz), 2.94 (1H, m), 2.69 (4H, q, J=11.55 Hz), 2.54 (1H, q, J=8.43 Hz), 2.17-2.02 (4H, m), 1.96-1.11 (14H, m), 0.93 (3H, t, J=6.96 Hz).

Example 15

2-[4-(2-Methoxymethyl-[1,3']bipyrrolidinyl-1'-yl)-phenyl]-8-oxa-2-aza-spiro[4.5]decan-1-one

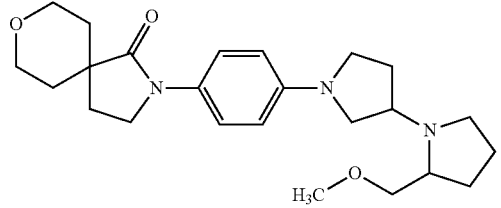

The title compound is synthesized following substantially the same procedures as set forth in Method B, Example 1 from 100 mg of the bromide to obtain 75.7 mg (57% yield) of the product as a brown gum.

LC $R_T$=1.95 min.; MS 414.

$^1$H NMR (300 MHz CDCl$_3$) δ 7.44 (2H, d, J=8.98 Hz), 6.53 (2H, d, J=8.98 Hz), 4.03 (2H, dt, J=11.73, 4.03 Hz), 3.74 (2H, t, J=6.78 Hz), 3.58 (2H, m), 3.51-3.16 (10H, m), 3.05 (1H, m), 2.93 (1H, m), 2.54 (1H, m), 2.30-1.66 (10H, m), 1.45 (2H, d, J=13.56 Hz).

Example 16

2-{4-[4-((S)-2-Methyl-pyrrolidin-1-yl)-piperidin-1-yl]-phenyl}-8-oxa-2-aza-spiro[4.5]decan-1-one

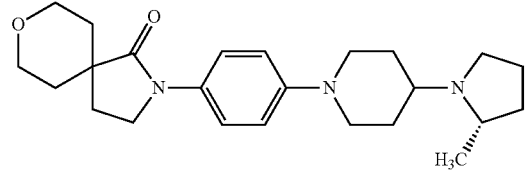

The title compound is synthesized following substantially the same procedures as set forth in Method B, Example 1 starting from 100 mg of the bromide to obtain 69.2 mg (54% yield) of the product as a brown gum.

LC $R_T$=1.86 min.; MS 398.

$^1$H NMR (300 MHz CDCl$_3$) δ: 7.50 (2H, d, J=8.98 Hz), 6.93 (2H, d, J=8.98 Hz), 4.02 (2H, dt, J=11.73, 4.03 Hz), 3.75 (2H, t, J=6.78 Hz), 3.69 (2H, d, J=12.10 Hz), 3.57 (2H, td, J=8.80, 2.38 Hz), 2.91 (2H, m), 2.78-2.53 (4H, m), 2.13 (2H, t, J=6.78 Hz), 2.06 (2H, m), 1.98-1.58 (7H, m), 1.44 (3H, d, J=12.38), 1.07 (3H, d, J=6.05 Hz).

Example 17

2-[3-Fluoro-4-(2-methyl-[1,3']bipyrrolidinyl-1'-yl)-phenyl]-9-oxa-2-aza-spiro[5.5]undecan-1-one

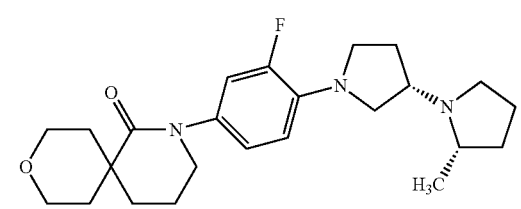

The title compound is synthesized following substantially the same procedures as set forth in Method B, Example 1 starting from 100 mg of the bromide to get 78.9 mg (65% yield) of the product as a brown gum.

LC $R_T$=2.42 min.; MS 416.

Example 18

2-{4-[4-(2-Ethyl-pyrrolidin-1-yl)-piperidin-1-yl]-2-trifluoromethyl-phenyl}-8-oxa-2-aza-spiro[4.5]decan-1-one

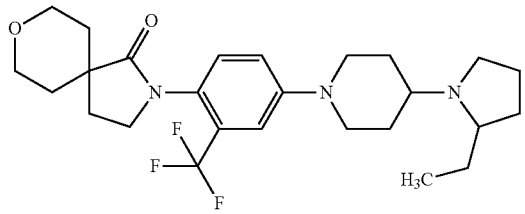

The title compound is synthesized following substantially the same procedures as set forth in Method B, Example 1 starting from 90 mg of the bromide to get 51.4 mg (45% yield) of the product as a brown gum.

LC $R_T$=2.37 min.; MS 480.

$^1$H NMR (300 MHz CDCl$_3$) δ: 7.18 (1H, s), 7.07 (2H, m), 4.03 (2H, dt, J=11.73, 4.03 Hz), 3.77 (2H, d, J=12.28 Hz), 3.61 (4H, m), 3.09-2.33 (5H, m), 2.18 (2H, t, J=6.78 Hz), 2.08 (2H, m), 1.96-1.40 (10H, m), 1.32-1.12 (3H, m), 0.88 (3H, t, J=7.33 Hz).

Example 19

2-{4-[4-(2-Isopropyl-pyrrolidin-1-yl)-piperidin-1-yl]-2-trifluoromethyl-phenyl}-8-oxa-2-aza-spiro[4.5]decan-1-one

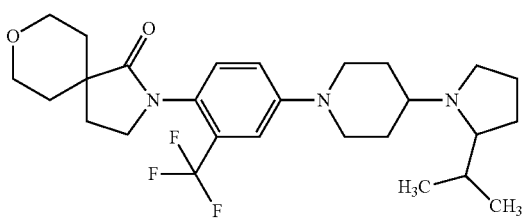

The title compound is synthesized following substantially the same procedures as set forth in Method B, Example 1 starting from 90 mg of the bromide to obtain 90 mg (76% yield) of the product as a brown gum.

LC $R_T$=2.38 min.; MS 494.

$^1$H NMR (300 MHz CDCl$_3$) δ: 7.17 (1H, d, J=2.38 Hz), 7.06 (2H, m), 4.03 (2H, m), 3.77 (2H, m), 3.61 (4H, m), 3.10-2.47 (5H, m), 2.78 (2H, t, J=6.96 Hz), 2.08 (2H, m), 2.00-1.44 (12H, m), 0.88 (6H, dd J=15.95, 6.96 Hz).

Example 20

2-[4-(2-Propyl[1,3']bipyrrolidinyl-1'-yl)-2-trifluoromethyl-phenyl]-8-oxa-2-aza-spiro[4.5]decan-1-one

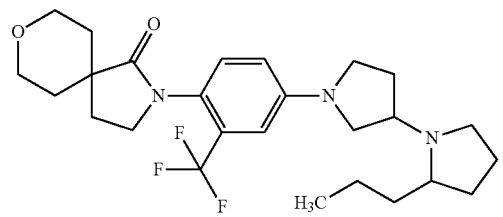

The title compound is synthesized following substantially the same procedures as set forth in Method B, Example 1 starting from 90 mg of the bromide to obtain 81.3 mg (71% yield) of the product as a brown gum.

LC $R_T$=2.44 min.; MS 480.

$^1$H NMR (300 MHz CDCl$_3$) δ: 7.05 (1H, d, J=8.61 Hz), 6.77 (1H, d, J=2.75 Hz), 6.65 (1H, dt, J=8.61, 2.75 Hz), 4.03 (2H, dt, J=11.55, 4.22 Hz), 3.59 (3H, m), 3.51-3.20 (4H, m), 2.99 (2H, m), 2.64 (1H, m), 2.52 (2H, m), 2.21-2.01 (4H, m), 1.97-1.67 (4H, m), 1.60-1.43 (4H, m), 1.41-1.18 (4H, m), 0.94 (3H, m).

Example 21

2-{4-[4-((S)-2-Methyl-pyrrolidin-1-yl)-piperidin-1-yl]-2-trifluoromethyl-phenyl}-8-oxa-2-aza-spiro[4.5]decan-1-one

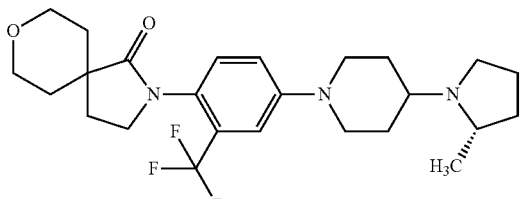

The title compound is synthesized following substantially the same procedures as set forth in Method B, Example 1 from 90 mg of the bromide to obtain 107.4 mg (96% yield) of the product as a brown gum.

LC $R_T$=2.19 min.; MS 466.

$^1$H NMR (300 MHz CDCl$_3$) δ: 7.18 (1H, s), 7.07 (2H, s), 4.03 (2H, dt, J=11.55, 4.22 Hz), 3.77 (2H, d, J=12.46 Hz), 3.61 (4H, m), 2.99-2.53 (6H, m), 2.17 (2H, t, J=6.78 Hz), 2.08 (2H, m), 2.02-1.56 (7H, m), 1.50 (3H, m), 1.07 (3H, d, J=6.23 Hz).

Example 22

2-[4-((2S,3'S)-2-Methyl-[1,3']bipyrrolidinyl-1'-yl)-2-trifluoromethyl-phenyl]-8-oxa-2-aza-spiro[4.5]decan-1-one

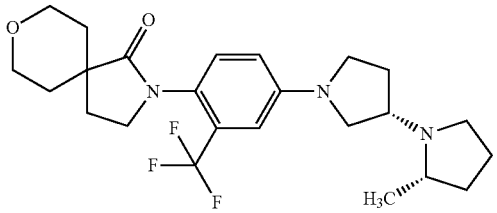

The title compound is synthesized following substantially the same procedures as set forth in Method B, Example 1 starting from 90 mg of the bromide to obtain 108 mg (100% yield) of the product as a brown gum.

LC $R_T$=2.18 min.; MS 452.

$^1$H NMR (300 MHz CDCl$_3$) δ: 7.05 (1H, d, J=8.61 Hz), 6.77 (1H, s), 6.66 (1H, d, J=8.61 Hz), 4.02 (2H, m), 3.69-3.21 (9H, m), 3.00 (1H, m), 2.81 (1H, m), 2.55 (1H, q, J=8.06 Hz), 2.23-1.90 (7H, m), 1.90-1.67 (2H, m), 1.49 (3H, d, J=13.93 Hz), 1.13 (3H, d, J=6.05 Hz).

Example 23

2-[4-((S)-2-Methyl-[1,4']bipiperidinyl-1'-yl)-2-trifluoromethyl-phenyl]-8-oxa-2-aza-spiro[4.5]decan-1-one

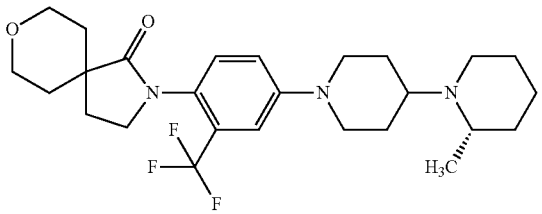

The title compound is synthesized following substantially the same procedures as set forth in Method B, Example 1 from 90 mg of the bromide to obtain 33.4 mg (29% yield) of the product as a brown gum.

LC $R_T$=2.37 min.; MS 480.

$^1$H NMR (300 MHz CDCl$_3$) δ: 7.17 (1H, s), 7.06 (2H, m), 4.03 (2H, m), 3.77 (2H, m), 3.58 (4H, m), 3.04-2.74 (4H, m), 2.61 (2H, m), 2.36-1.88 (8H, m), 1.87-1.21 (8H, m), 1.11 (3H, t, J=6.23 Hz).

Example 24

2-{2-Ethyl-4-[4-(2-propyl-pyrrolidin-1-yl)-piperidin-1-yl]-phenyl}-8-oxa-2-aza-spiro[4.5]decan-1-one

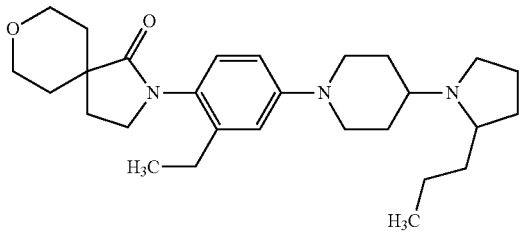

The title compound is synthesized following substantially the same procedures as set forth in Method B, Example 1 starting from 77 mg of the bromide to get 84.6 mg (81% yield) of the product a brown gum.

LC $R_T$=2.29 min.; MS 454.

$^1$H NMR (300 MHz CDCl$_3$) δ: 6.95 (1H, d, J=8.43 Hz), 6.79 (2H, m), 4.04 (2H, dt, J=11.55, 4.03 Hz), 3.72 (2H, d, J=10.81 Hz), 3.60 (4H, m), 3.13 (1H, d, J=11.55 Hz), 2.94 (1H, m), 2.81-2.41 (8H, m), 2.22-2.05 (4H, m), 1.96-1.61 (8H, m), 1.49 (2H, m), 1.43-1.22 (2H, m), 1.18 (3H, t, J=7.51 Hz), 0.93 (3H, m).

Example 25

2-{2-Ethyl-4-[4-(2-methoxymethyl-pyrrolidin-1-yl)-piperidin-1-yl]-phenyl}-8-oxa-2-aza-spiro[4.5]decan-1-one

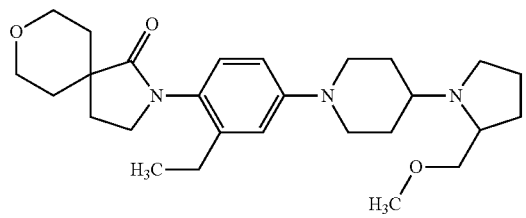

The title compound is synthesized following substantially the same procedures as set forth in Method B, Example 1 starting from 77 mg of the bromide to obtain 82.9 mg (81% yield) of the product as a brown gum.

LC $R_T$=1.97 min.; MS 456.

$^1$H NMR (300 MHz CDCl$_3$) δ: 6.96 (1H, d, J=8.43 Hz), 6.79 (2H, m), 4.04 (2H, dt, J=11.55, 3.85 Hz), 3.71 (2H, d, J=11.91 Hz), 3.60 (4H, m), 3.35 (3H, m), 3.18 (1H, m), 3.01 (3H, m), 2.81-2.41 (6H, m), 2.15 (4H, m), 2.00-1.43 (10H, m), 1.18 (3H, t, J=7.70 Hz).

Example 26

2-[2-Ethyl-4-((2S,3'S)-2-methyl-[1,3']bipyrrolidinyl-1'-yl)-phenyl]-8-oxa-2-aza-spiro[4.5]decan-1-one

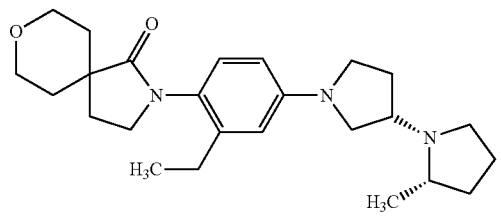

The title compound is synthesized following substantially the same procedures as set forth in Method B, Example 1 starting from 77 mg of the bromide to obtain 94.1 mg (99% yield) of the product as a brown gum.

LC $R_T$=1.98 min.; MS 426.

$^1$H NMR (300 MHz CDCl$_3$) δ: 6.93 (1H, d, J=8.25 Hz), 6.40 (2H, m), 4.03 (2H, dt, J=11.73, 4.03 Hz), 3.59 (4H, m), 3.40 (1H, m), 3.27 (3H, m), 3.02 (1H, m), 2.79 (1H, m), 2.61-2.42 (3H, m), 2.14 (4H, m), 1.99 (1H, m), 1.89-1.65 (5H, m), 1.48 (3H, d, J=12.83 Hz), 1.19 (3H, t, J=7.51 Hz), 1.14 (3H, d, J=6.23 Hz)

Example 27

2-[2-Fluoro-4-((2S,3'S)-2-methyl-[1,3']bipyrrolidinyl-1'-yl)-phenyl]-9-oxa-2-aza-spiro[5.5]undecan-1-one

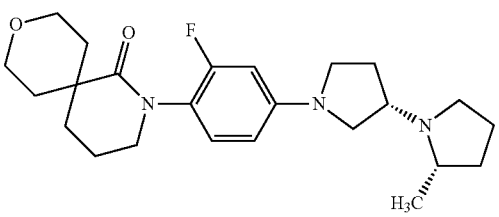

Step 1: 4-{3-[2-Fluoro-4-((2S,3'S)-2-methyl-[1,3']bipyrrolidinyl-1'-yl)-phenylamino]-propyl}-tetrahydro-pyran-4-carboxylic acid methyl ester

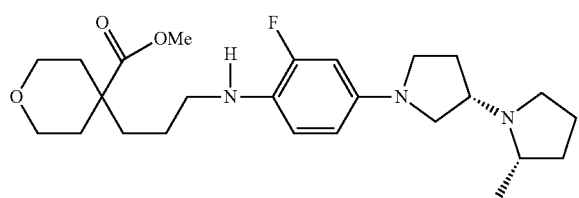

4-(3-Oxo-propyl)tetrahydro-pyran-4-carboxylic acid methyl ester (135 mg, 0.515 mmol, 1 eq) was dissolved in 2.4 mL of 1,2-dichloroethane. To this was added 2-Fluoro-4-((2S,3'S)-2-methyl-[1,3']bipyrrolidinyl-1'-yl)-phenylamine (103 mg, 0.515 mmol, 1 eq) in 6.2 mL of 1,2-dichloroethane. To the combined mixture was added glacial acetic acid (96 mg, 1.6 mmol, 3.1 eq) followed by NaBH(OAc)$_3$ (330 mg, 1.55 mmol, 3 eq). The reaction mixture was stirred at rt for 15 h. The reaction mixture was quenched with water, transferred to a separatory funnel and extracted with CH-2Cl2 (2×100 mL). The combined organics were dried over Na$_2$SO$_4$, concentrated under vacuum and purified by column chromatography on silica gel (40 g column, 6% MeOH in CH$_2$Cl$_2$; 35 mL/min). This gave 130 mg (61%) of the title compound as a beige semi-solid.

Step 2

4-{3-[2-Fluoro-4-((2S,3'S)-2-methyl-[1,3']bipyrrolidinyl-1'-yl)-phenylamino]-propyl}-tetrahydro-pyran-4-carboxylic acid methyl ester (40 mg, 0.1 mmol, 1 eq) was dissolved in 2 mL of THF and cooled to 0° C., where a 2.5 M solution of n-BuLi in heptanes (0.11 mL, 0.17 mmol, 3 eq) was added drop-wise and the ice bath was removed. After 30 min the reaction mixture was quenched with water, transferred to a separatory funnel and extracted with diethyl ether (2×50 mL). The combined organics were dried over Na2SO4 and purified by column chromatography on silica gel (40 g column, 10% MeOH in CH2Cl2; 35 mL/min). This gave 38 mg (98%) of the title compound as an off-white gum.

LC/MS: $R_T$=1.89 min, MS: 416.

$^1$H NMR (300 MHz CDCl$_3$) δ: 6.99 (m, 1H), 6.29 (m, 2H), 3.98 (m, 2H), 3.69 (m, 2H), 3.54 (m, 2H), 3.47 (m, 1H), 3.35 (m, 1H), 3.31-3.15 (m, 3H), 3.00 (m, 1H), 2.77 (m, 1H), 2.52 (q, 8.4 Hz, 1H), 2.21 (m, 3H), 2.10-1.68 (m, 8H), 1.50 (m, 3H), 1.13 (d, 6.3 Hz, 3H).

Example 28

2-[2-Methyl-4-((2R,3'S)-2-methyl-[1,3']bipyrrolidinyl-1'-yl)-phenyl]-9-oxa-2-aza-spiro[5.5]undecan-1-one

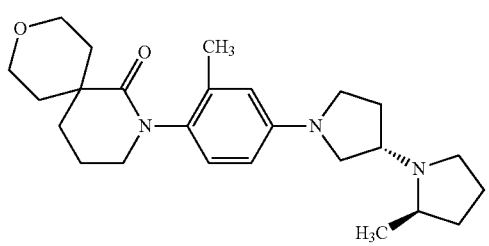

The HCl salt of (2R,3'S)-2-Methyl-[1,3']bipyrrolidinyl was dissolved in 2 mL of MeOH with the aid of sonication. To the solution was added 50 mL of DCM. The solution was cooled to an ice-water bath. To this solution was added powder KOH (0.5 g, 9.5 mmol, 2.6 equiv. to the amine salt) with stirring under N$_2$. The stirring was continued for 1 h. 0.5 g of powder K$_2$CO$_3$ was added with stirring to form a nice suspension. The suspension was filtered through a Celite pad, rinsed with DCM until no amine was leach out by TLC (20% MeOH in DCM, anisaldehyde visualization, white spot just above the origin). The solution was concentrated to dryness; the residue was further dried under high vacuum with stirring for 1 h, re-dissolved in anhydrous toluene and ready to use.

An 20-mL vial containing a stir bar was charged with Pd$_2$(dba)$_3$ (0.01 equiv., 0.002036 mmol, 2 mg.), 2-dicyclohexylphosphino-2',4',6'-triisopropylbiphenyl 1 (0.05 equiv., 0.01018 mmol, 4.85 mg.), 2-(4-bromo-2-methyl-phenyl)-9-oxa-2-aza-spiro[5.5]undecan-1-one (1 equiv. 66 mg, 0.2036 mmol), and sodium t-butoxide (2.5 equiv., 0.509 mmol, 0.4891 g.). The vial was de-gassed and refilled with N$_2$ three cycles. 100 mL of anhydrous toluene was introduced and the red solution was stirred for 2 min at rt, then the amine (1.11 equiv., 22.71 mmol, obtained from above) in toluene was introduced into the flask via cannula. The flask was evacuated and backfilled with N2. The reaction was heated in an oil bath set at 90° C. for 2.5 h, allowed to cool down to room temperature and quenched with water (2 mL) and extracted with DCM (3×100 mL). The combined DCM extracts were washed with sodium bicarbonate (50 mL), and brine (50 mL), dried (anhydrous potassium carbonate), filtered, and concentrated. The crude product was purified on a 10-g silica gel column eluted with DCM and 5% of 7N NH$_3$MeOH in DCM to get the titled compound.

LC/MS: $R_T$=1.96 min, MS: 412

$^1$H NMR (300 MHz CDCl$_3$) δ: 6.93 (1H, d, J=8.25 Hz), 6.40 (2H, m), 4.03 (2H, dt, J=11.73, 4.03 Hz), 3.59 (4H, m), 3.40 (1H, m), 3.27 (3H, m), 3.02 (1H, m), 2.79 (1H, m), 2.61-2.42 (3H, m), 2.14 (4H, m), 1.99 (1H, m), 1.89-1.65 (5H, m), 1.48 (3H, d, J=12.83 Hz), 1.19 (3H, t, J=7.51 Hz), 1.14 (3H, d, J=6.23 Hz).

Example 29

2-[2-Methyl-4-((2R,3'R)-2-methyl-[1,3']bipyrrolidi-nyl-1'-yl)-phenyl]-8-oxa-2-aza-spiro[4.5]decan-1-one

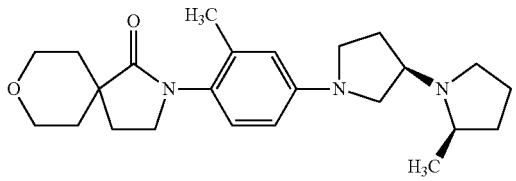

The title compound is synthesized following substantially the same procedures as set forth in Method B, Example 1 from corresponding starting materials.

LC $R_T$=1.95 min.; MS 398.

$^1$H NMR (300 MHz CDCl$_3$) δ 6.94 (m, 1H), 6.39 (m, 2H), 4.05 (dt, 4.2 Hz, 11.7 Hz, 2H), 3.64-3.47 (m, 10H), 3.37 (dt, 2.6 Hz, 9.0 Hz, 1H), 2.76 (sixtet, 6.3 Hz, 1H), 2.52 (q, 8.4 Hz, 1H), 2.14 (s, 3H), 2.12 (m, 4H), 1.98 (m, 2H), 1.77 (m, 2H), 1.48 (m, 3H), 1.14 (d, 6.3 Hz, 3H).

Example 30

2-[2-Methyl-4-((2S,3'R)-2-methyl-[1,3']bipyrrolidi-nyl-1'-yl)-phenyl]-8-oxa-2-aza-spiro[4.5]decan-1-one

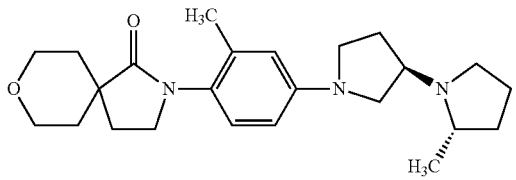

The title compound is synthesized following substantially the same procedures as set forth in Method B, Example 1 from corresponding starting materials.

LC $R_T$=1.95 min.; MS 398.

$^1$H NMR (300 MHz CDCl$_3$) δ 6.96 (m, 1H), 6.39 (m, 2H), 4.05 (dt, 4.2 Hz, 11.4 Hz, 2H), 3.64-3.47 (m, 10H), 3.37 (dt, 3.6 Hz, 9.0 Hz, 1H), 2.79 (sixtet, 6.3 Hz, 1H), 2.56 (q, 8.4 Hz, 1H), 2.17 (m, 4H), 2.14 (s, 3H), 1.98-1.69 (m, 4H), 1.48 (m, 3H), 1.14 (d, 6.3 Hz, 3H).

Example 31

2-[2-Methyl-4-(2-methyl-[1,3']bipyrrolidinyl-1'-yl)-phenyl]-8-oxa-2-aza-spiro[4.5]decan-1-one

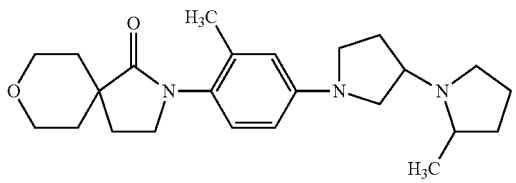

The title compound is synthesized following substantially the same procedures as set forth in Method B, Example 1 from corresponding starting materials.

LC $R_T$=1.96 min.; MS 398.

$^1$H NMR (300 MHz CDCl$_3$)—exhibits twos sets of spectra.

Example 32

2-[2-Methyl-4-((2R,3'R)-2-methyl-[1,3']bipyrrolidi-nyl-1'-yl)-phenyl]-9-oxa-2-aza-spiro[5.5]undecan-1-one

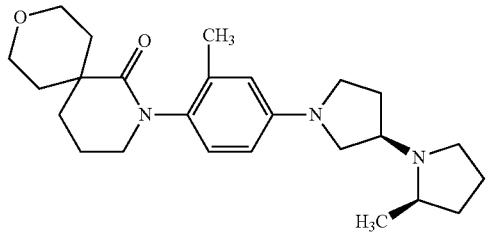

The title compound is synthesized following substantially the same procedures as set forth in Method B, Example 1 from corresponding starting materials.

LC $R_T$=1.85 min.; MS 412.

$^1$H NMR (300 MHz CDCl$_3$) δ 6.94 (m, 1H), 6.39 (m, 2H), 3.98 (m, 2H), 3.77-3.16 (m, 9H), 3.00 (m, 1H), 2.797 (sixtet, 6.9 Hz, 1H), 2.52 (q, 8.4 Hz, 1H), 2.24 (m, 3H), 2.10 (s, 3H), 2.04-1.68 (m, 8H), 1.60-1.41 (m, 3H), 1.13 (d, 6.3 Hz, 3H).

Example 33

2-[2-Methyl-4-((2S,3'R)-2-methyl-[1,3']bipyrrolidi-nyl-1'-yl)-phenyl]-9-oxa-2-aza-spiro[5.5]undecan-1-one

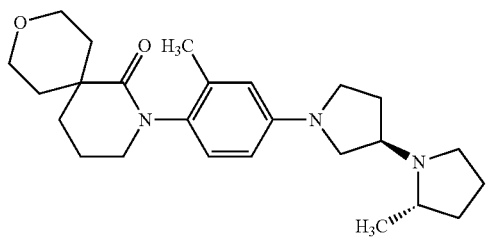

The title compound is synthesized following substantially the same procedures as set forth in Method B, Example 1 from corresponding starting materials.

LC $R_T$=1.91 min.; MS 412.

$^1$H NMR (300 MHz CDCl$_3$) δ 6.93 (m, 1H), 6.40 (m, 2H), 3.98 (m, 2H), 3.73-3.51 (m, 3H), 3.44-3.19 (m, 6H), 2.98 (m, 1H), 2.79 (sixtet, 6.9 Hz, 1H), 2.53 (q, 8.4 Hz, 1H), 2.33-2.16 (m, 3H), 2.10 (s, 3H), 2.05-1.65 (m, 8H), 1.60-1.41 (m, 3H), 1.14 (d, 6.3 Hz, 3H).

Example 34

2-[4-((2R,3'S)-2-Methyl-[1,3']bipyrrolidinyl-1'-yl)-phenyl]-9-oxa-2-aza-spiro[5.5]undecan-1-one

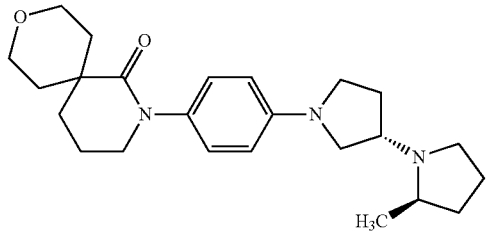

The title compound is synthesized following substantially the same procedures as set forth in Method B, Example 1 from corresponding starting materials.

LC $R_T$=1.75 min.; MS 398.

Example 35

2-[4-((2R,3'R)-2-Methyl-[1,3']bipyrrolidinyl-1'-yl)-phenyl]-9-oxa-2-aza-spiro[5.5]undecan-1-one

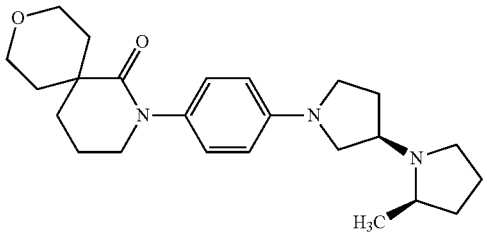

The title compound is synthesized following substantially the same procedures as set forth in Method B, Example 1 from corresponding starting materials.

LC $R_T$=1.83 min.; MS 398.

$^1$H NMR (300 MHz CDCl$_3$) δ 7.04 (d, 8.7 Hz, 2H), 6.54 (d, 8.7 Hz, 2H), 3.98 (m, 2H), 3.68 (m, 2H), 3.59 (m, 2H), 3.44-3.20 (m, 5H), 3.01 (m, 1H), 2.77 (m, 1H), 2.53 (q, 8.4 Hz, 1H), 2.23 (m, 3H), 2.18-1.67 (m, 8H), 1.50 (m, 3H), 1.14 (d, 6.3 Hz, 3H).

Example 36

2-[4-((2S,3'R)-2-Methyl-[1,3']bipyrrolidinyl-1'-yl)-phenyl]-9-oxa-2-aza-spiro[5.5]undecan-1-one

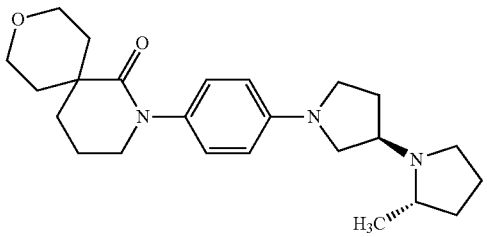

The title compound is synthesized following substantially the same procedures as set forth in Method B, Example 1 from corresponding starting materials.

LC $R_T$=1.85 min.; MS 398.

$^1$H NMR (300 MHz CDCl$_3$) δ 7.04 (d, 8.7 Hz, 2H), 6.54 (d, 8.7 Hz, 2H), 3.98 (m, 2H, 3.73-3.56 (m 4H), 3.44-3.20 (m, 5H), 2.98 (m, 1H), 2.79 (m, 1H), 2.53 (q, 8.4 Hz, 1H), 2.23 (m, 3H), 2.08-1.69 (m, 8H), 1.49 (m, 3H), 1.14 (d, 6.3 Hz, 3H).

Example 37

2-[4-((2S,3'S)-2-Methyl-[1,3']bipyrrolidinyl-1'-yl)-phenyl]-9-oxa-2-aza-spiro[5.5]undecan-1-one

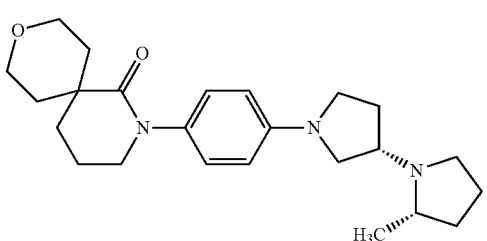

The title compound is synthesized following substantially the same procedures as set forth in Method B, Example 1 from corresponding starting materials.

LC $R_T$=1.83 min.; MS 398.

$^1$H NMR (300 MHz CDCl$_3$) δ 7.04 (d, 8.7 Hz, 2H), 6.54 (d, 8.7 Hz, 2H), 3.98 (m, 2H), 3.68 (m, 2H), 3.59 (m, 2H), 3.44-3.20 (m, 5H), 3.01 (m, 1H), 2.77 (m, 1H), 2.53 (q, 8.4 Hz, 1H), 2.23 (m, 3H), 2.18-1.67 (m, 8H), 1.50 (m, 3H), 1.14 (d, 6.3 Hz, 3H).

Example 38

2-[2-Fluoro-4-((2R,3'S)-2-Methyl-[1,3']bipyrrolidinyl-1'-yl)-phenyl]-9-oxa-2-aza-spiro[5.5]undecan-1-one

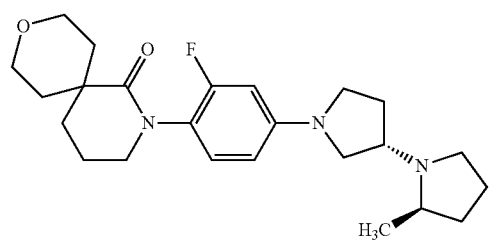

The title compound is synthesized following substantially the same procedures as set forth in Method B, Example 1 from corresponding starting materials.

LC $R_T$=1.89 min.; MS 416.

$^1$H NMR (300 MHz CDCl$_3$) δ 6.99 (m, 1H), 6.29 (m, 2H), 3.98 (m, 2H), 3.69 (m, 2H), 3.54 (m, 2H), 3.43-3.16 (m, 5H), 2.97 (dt, 3.6 Hz, 7.8 Hz, 1H), 2.79 (sixtet, 6.0 Hz, 1H), 2.52 (q, 8.4 Hz, 1H), 2.21 (m, 3H), 2.10-1.68 (m, 8H), 1.50 (m, 3H), 1.14 (d, 6.3 Hz, 3H).

Example 39

2-[2-Fluoro-4-((2R,3'R)-2-Methyl-[1,3']bipyrrolidinyl-1'-yl)-phenyl]-9-oxa-2-aza-spiro[5.5]undecan-1-one

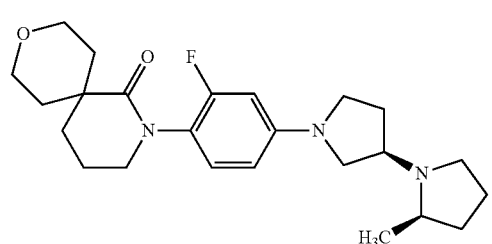

The title compound is synthesized following substantially the same procedures as set forth in Method B, Example 1 from corresponding starting materials.

LC $R_T$=1.93 min.; MS 416.

$^1$H NMR (300 MHz CDCl$_3$) δ 6.99 (m, 1H), 6.29 (m, 2H), 3.98 (m, 2H), 3.69 (m, 2H), 3.54 (m, 2H), 3.47 (m, 1H), 3.35 (m, 1H), 3.31-3.15 (m, 3H), 3.00 (m, 1H), 2.77 (m, 1H), 2.52 (q, 8.4 Hz, 1H), 2.21 (m, 3H), 2.10-1.68 (m, 8H), 1.50 (m, 3H), 1.13 (d, 6.3 Hz, 3H).

Example 40

2-[2-Fluoro-4-((2S,3'R)-2-Methyl-[1,3']bipyrrolidinyl-1'-yl)-phenyl]-9-oxa-2-aza-spiro[5.5]undecan-1-one

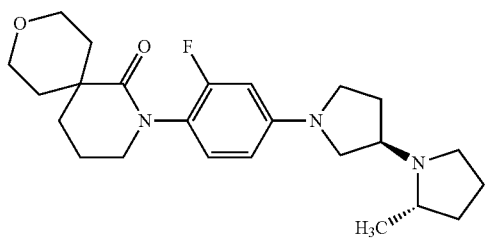

The title compound is synthesized following substantially the same procedures as set forth in Method B, Example 1 from corresponding starting materials.

LC $R_T$=1.95 min.; MS 416.

$^1$H NMR (300 MHz CDCl$_3$) δ 6.99 (m, 1H), 6.29 (m, 2H), 3.98 (m, 2H), 3.69 (m, 2H), 3.54 (m, 2H), 3.43-3.16 (m, 5H), 2.97 (dt, 3.6 Hz, 7.8 Hz, 1H), 2.79 (sixtet, 6.0 Hz, 1H), 2.52 (q, 8.4 Hz, 1H), 2.21 (m, 3H), 2.10-1.68 (m, 8H), 1.50 (m, 3H), 1.14 (d, 6.3 Hz, 3H).

BIOLOGICAL EXAMPLES

Example 41

This Example 41 demonstrates the efficacy of the compounds of this invention as H3 receptor ligands. The compounds of this invention have been demonstrated to displace [$^3$H]-methylhistamine radioligand binding to mammalian cell membranes expressing rhesus (*Macacca Mulatta*) H3 receptor. These compounds display rhesus H3 affinity constants (Ki) in the range of 1 μM to <1 nM. Additionally, the compounds of this invention have been demonstrated by GTPγS radioligand binding assay to inhibit rhesus H3 constitutive functional activity in cell membranes. This inhibition of basal rhesus H3-mediated GTPγS radioligand binding demonstrates that the compounds of this invention find utility as inverse agonists. These compounds decreased rhesus H3 GTPγS radioligand binding by 0-40% below basal levels.

Rhesus H3 membranes were prepared from the Flp-In T-REx 293 Cell Line (Invitrogen) stably transfected with pcDNA5/FRT/TO (Invitrogen) containing the rhesus monkey (*Macacca Mulatta*) 445 amino acid H3 receptor. (Genbank #AY231164). Stably transfected cultures were amplified in tissue culture flasks by standard tissue culture methods and induced to express rhesus H3 by exposure to 500 ng/ml tetracycline (Cellgro) for 24 hours. After induction, cells were dissociated from flasks utilizing Cell Stripper (Cellgro). Cells were centrifuged (1 K×g, 5 min) and pellet frozen in an ethanol-dry ice bath to disrupt cell membranes. Frozen cell pellet was re-suspended in 5 mM HEPES (pH 7.4, Invitrogen) at 10 ml/1000 cm2 of harvested cells. The cell suspension was drawn through an 18 gauge needle (2-3x) followed by a 23 gauge needle (2-3x) to further disrupt cell membranes. The cell suspension was centrifuged (40K×g, 30 min). Cell membrane pellet was re-suspended in 5 mM HEPES (pH 7.4, Invitrogen) at a final protein concentration of 10 mg/ml. Rhesus H3 membranes were stored under liquid nitrogen prior to use in [3H]-Methylhistamine and GTP S radioligand binding assays.

Rhesus H3 radioligand binding assay was performed using rhesus H3 receptor membranes (prepared as described above), [3H]-Methylhistamine (Perkin Elmer) and WGA SPA beads (wheat germ agglutinin scintillation proximity assay) beads (Amersham). The assay was performed in 96-well Opti-Plates (Packard). Each reaction contained 50 μl rhesus H3 membranes (20-30 μg total protein), 50 μl WGA SPA beads (0.1 μg) and 50 μl of 83 Ci/mmol [$^3$H]-Methylhistamine (final concentration 2 nM) and 50 μl of tested compound. The compounds of this invention and/or vehicle were diluted with binding buffer from 10 mM DMSO stocks. Assay plates were sealed with TopSeal (Perkin Elmer) and mixed on shaker (25° C., 1 hour). Assay plates were read on TopCount scintillation counter (Packard). Results were analyzed by Hill transformation and Ki values were determined by Cheng-Prusoff equation. The observed binding data for a few of the representative compounds of this invention are summarized in Table 1.

TABLE 1

| Example No. | Rhesus H3 binding ki (nM) | Inverse Agonism: % inhibition of Basal GTPγS binding in Rhesus H3 |
|---|---|---|
| 1 | 0.93 | −25 |
| 2 | 0.38 | −9 |
| 3 | 0.63 | −26 |
| 4 | 2.1 | −31 |
| 5 | 0.7 | −11 |
| 6 | 38 | −36 |
| 7 | 5.2 | −35 |
| 8 | 76 | −22 |
| 9 | 170 | −30 |
| 10 | 0.16 | −33 |
| 11 | 0.45 | −11 |
| 12 | 0.45 | −22 |
| 13 | 16 | −22 |
| 14 | 13 | −33 |
| 15 | 190 | −26 |
| 16 | 0.52 | −29 |
| 17 | 2.5 | −16 |
| 18 | 4.3 | −35 |
| 19 | 100 | −8 |
| 20 | 650 | −12 |
| 21 | 0.42 | −19 |
| 22 | 8.6 | −21 |
| 23 | 1.5 | −29 |
| 24 | 18 | −18 |
| 25 | 4.9 | −13 |
| 26 | 0.13 | −14 |
| 27 | 0.7 | −20 |
| 28 | 13 | −13 |
| 29 | 28 | −28 |
| 30 | 4.3 | −29 |
| 31 | 6.2 | −28 |
| 32 | 11 | −15 |
| 33 | 1.4 | −19 |
| 34 | 1.7 | −12 |
| 35 | 0.7 | −13 |
| 36 | 0.26 | −10 |
| 37 | 0.1 | −20 |
| 38 | 1.3 | −22 |
| 39 | 0.75 | −13 |
| 40 | 0.09 | −18 |

Example 42

This Example illustrates the study of efficacy of the compounds of this invention in increasing the wakefulness in animal models.

Male Sprague Dawley rats (Charles River, France) weighing 250±10 g were anaesthetized with ZOLETIL® 50 (60 mg/kg ip) and mounted in a stereotaxic apparatus. Cortical electrodes (small stainless steel screw electrodes of 0.9 mm in diameter) were screwed into the bone over the sensorimotor cortex (1.5 mm lateral to the median suture and 1.5 mm behind the fronto-parietal suture), the visual cortex (1.5 mm lateral to the median suture and 1.5 mm in front of the parieto-occipital suture) and over the cerebellum (reference electrode). Cortical electrodes were attached to a connector (Winchester, 7-lead) and fixed with dental cement to the cranium.

After three weeks of post-operative recovery, animals were placed in plexiglass cylinders (60 cm diameter) with free access to food and water. The temperature of the room was kept constant (21±1° C.) and lights were on from 7 a.m. to 7 p.m. The rats were recorded from 10 a.m. to 4 p.m. during three consecutive days: control day (D1), drug day (D2) and post drug day (D3). Vehicle (D1 and D3) or drug (D2) were administered 15 min before the recording.

Activity in sensorimotor and visual cortices were recorded by comparison with the reference electrode placed over the cerebellar cortex. Three stages were differentiated:
wakefulness (W) characterized by low voltage fast electrocortical (ECoG) activity;
NREM sleep (non rapid eye movement or slow wave sleep: SWS) characterized by an increase in electrocortical activity; development of high-amplitude slow waves with some bursts of sleep spindles;
REM sleep (rapid eye movement or paradoxical sleep: PS) characterized by hypersynchronization of the theta rhythm in the visual area.

Analysis of the ECoG signal was performed automatically by means of a computerized system discriminating between the various sleep phases using sequential spectral analysis of ten seconds periods (Deltamed's software "Coherence"). The compounds of this invention were dissolved in 0.6% MTC tween and administered by oral route (po). The volume of injection was 0.5 ml/100 g of body weight.

Two types of analysis were used to quantify the effects of the compounds of this invention on sleep-wakefulness variables: the one hour-period and the six hour-period analysis.

The results are expressed in minutes (one hour-period analysis) or as the percentage of the control values (100%). Statistical analysis of the data was carried out using the Student's t test for paired values to determine significant variations from control values.

Example 43

Stress-Induced Ultrasonic Vocalizations Test in Adult Rats

This Example illustrates the study of efficacy of the compounds of this invention as antidepressive agents in animal models.

The procedure used was adapted from the technique described by Van Der Poel A. M, Noach E. J. K, Miczek K. A (1989) Temporal patterning of ultrasonic distress calls in the adult rat: effects of morphine and benzodiazepines. *Psychopharmacology* 97:147-8. Rats were placed for a training session in a cage with a stainless steel grid floor (MED Associates, Inc., St. Albans, Vt.). Four electric shocks (0.8 mA, 3 s) were delivered every 7 s and ultrasonic vocalizations (UV, 22 KHz) were subsequently recorded with the Ultravox system (Noldus, Wageningen, The Netherlands) during 2 min. A modified ultrasound detector (Mini-3 bat model) connected to a microphone was used to transform ultrasonic sound into audible sound. The signal was then filtered and sent to a computer where the Ultravox software recorded each bout of UV that lasted more than 10 ms. Rats were selected on the basis of their UV duration (>40 s) and subjected to the test, 4 h after training. For the test, rats were placed in the same cage as that used for training. One electric shock (0.8 mA, 3 s) was delivered and UV (duration and frequency) were subsequently recorded with the Ultravox system during 2 min. The compounds of this invention were administered p.o. 60 min before testing.

Example 44

Forced-Swimming Test in Rats

This Example further illustrates the study of efficacy of the compounds of this invention as antidepressive agents in animal models.

The procedure was a modification of that described by Porsolt et al. (1977) Depression: a new animal model sensitive to antidepressant treatments. *Nature* 266:730-2. Rats were placed in individual glass cylinder (40 cm height, 17 cm diameter) containing water (21° C.) to a height of 30 cm. Two swimming sessions were conducted (a 15-min training session followed 24 h later by a 6-min test). After each swimming session, rats were placed under a heating lamp to avoid hypothermia. The duration of immobility was measured during the 6-min test. The compounds of this invention were administered p.o. twice (15 min after training session and 60 min before the test).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of formula (I):

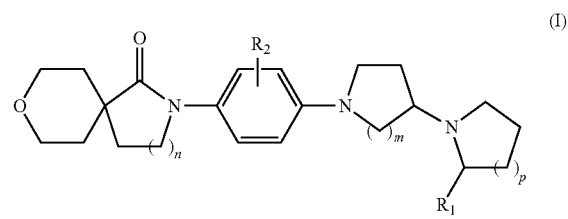

wherein
m is 1 or 2;
n is 1 or 2;
p is 1 or 2;
$R_1$ is hydrogen, $(C_1-C_4)$alkyl, $CF_3$, or $(C_1-C_4)$alkoxy-$(C_1-C_4)$alkyl; and
$R_2$ is hydrogen, halogen, $(C_1-C_4)$alkyl or $CF_3$; or
a salt thereof or an enantiomer or a diastereomer thereof.
2. The compound according to claim 1, wherein
n, m and p are 1;
$R_1$ is methyl, ethyl, isopropyl, n-propyl or methoxymethyl; and
$R_2$ is hydrogen, fluorine, chlorine, methyl, ethyl or $CF_3$; or
a salt thereof or an enantiomer or a diastereomer thereof.
3. The compound according to claim 1, wherein
n is 2 and m is 1; or
n is 1 and m is 2;
p is 1 or 2;

R₁ is methyl, ethyl, isopropyl, n-propyl or methoxymethyl; and

R₂ is hydrogen, fluorine, chlorine, methyl, ethyl or CF₃; or a salt thereof or an enantiomer or a diastereomer thereof.

4. The compound of claim 1 selected from the group consisting of:

2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[3-fluoro-4-((2S,3'S)-2-methyl-[1,3']bipyrrolidinyl-1'-yl)-phenyl]-8-oxa-2-aza-spiro[4.5]decan-1-one;
2-{2-methyl-4-[4-((S)-2-methyl-pyrrolidin-1-yl)-piperidin-1-yl]-phenyl}-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-[4-(2-ethyl-[1,3']bipyrrolidinyl-1'-yl)-2-fluoro-phenyl]-8-oxa-2-aza-spiro[4.5]decan-1-one;
2-[2-fluoro-4-(2-isopropyl-[1,3']bipyrrolidinyl-1'-yl)-phenyl]-8-oxa-2-aza-spiro[4.5]decan-1-one;
2-[2-fluoro-4-(2-propyl-[1,3']bipyrrolidinyl-1'-yl)-phenyl]-8-oxa-2-aza-spiro[4.5]decan-1-one;
2-{2-fluoro-4-[4-((S)-2-methyl-pyrrolidin-1-yl)-piperidin-1-yl]-phenyl}-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((S)-2-methyl-[1,4']bipiperidinyl-1'-yl)-phenyl]-8-oxa-2-aza-spiro[4.5]decan-1-one;
2-{4-[4-(2-isopropyl-pyrrolidin-1-yl)-piperidin-1-yl]-phenyl}-8-oxa-2-aza-spiro[4.5]decan-1-one;
2-{4-[4-(2-propyl-pyrrolidin-1-yl)-piperidin-1-yl]-phenyl}-8-oxa-2-aza-spiro[4.5]decan-1-one;
2-[4-(2-methoxymethyl-[1,3']bipyrrolidinyl-1'-yl)-phenyl]-8-oxa-2-aza-spiro[4.5]decan-1-one;
2-{4-[4-((S)-2-methyl-pyrrolidin-1-yl)-piperidin-1-yl]-phenyl}-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;
2-{4-[4-(2-ethyl-pyrrolidin-1-yl)-piperidin-1-yl]-2-trifluoromethyl-phenyl}-8-oxa-2-aza-spiro[4.5]decan-1-one;
2-{4-[4-(2-isopropyl-pyrrolidin-1-yl)-piperidin-1-yl]-2-trifluoromethyl-phenyl}-8-oxa-2-aza-spiro[4.5]decan-1-one;
2-[4-(2-propyl-[1,3']bipyrrolidinyl-1'-yl)-2-trifluoromethyl-phenyl]-8-oxa-2-aza-spiro[4.5]decan-1-one;
2-{4-[4-((S)-2-methyl-pyrrolidin-1-yl)-piperidin-1-yl]-2-trifluoromethyl-phenyl}-8-oxa-2-aza-spiro[4.5]decan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[4-((S)-2-methyl-[1,4']bipiperidinyl-1'-yl)-2-trifluoromethyl-phenyl]-8-oxa-2-aza-spiro[4.5]decan-1-one;
2-{2-ethyl-4-[4-(2-propyl-pyrrolidin-1-yl)-piperidin-1-yl]-phenyl}-8-oxa-2-aza-spiro[4.5]decan-1-one;
2-{2-ethyl-4-[4-(2-methoxymethyl-pyrrolidin-1-yl)-piperidin-1-yl]-phenyl}-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3'S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;
2-[2-methyl-4-(2-methyl-[1,3']bipyrrolidinyl-1'-yl)-phenyl]-8-oxa-2-aza-spiro[4.5]decan-1-one;
2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one; or a salt thereof or an enantiomer or a diastereomer thereof.

5. The compound of claim 1 selected from the group consisting of:

2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[3-fluoro-4-((2S,3'S)-2-methyl-[1,3']bipyrrolidinyl-1'-yl)-phenyl]-8-oxa-2-aza-spiro[4.5]decan-1-one;
2-{2-methyl-4-[4-((S)-2-methyl-pyrrolidin-1-yl)-piperidin-1-yl]-phenyl}-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-{2-fluoro-4-[4-((S)-2-methyl-pyrrolidin-1-yl)-piperidin-1-yl]-phenyl}-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((S)-2-methyl-[1,4']bipiperidinyl-1'-yl)-phenyl]-8-oxa-2-aza-spiro[4.5]decan-1-one;
2-{4-[4-((S)-2-methyl-pyrrolidin-1-yl)-piperidin-1-yl]-phenyl}-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;
2-{4-[4-((S)-2-methyl-pyrrolidin-1-yl)-piperidin-1-yl]-2-trifluoromethyl-phenyl}-8-oxa-2-aza-spiro[4.5]decan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[4-((S)-2-methyl-[1,4']bipiperidinyl-1'-yl)-2-trifluoromethyl-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3+S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;

2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one; or
a salt thereof or an enantiomer or a diastereomer thereof.

6. The compound of claim 1 selected from the group consisting of:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[3-fluoro-4-((2S,3'S)-2-methyl-[1,3']bipyrrolidinyl-1'-yl)-phenyl]-8-oxa-2-aza-spiro[4.5]decan-1-one;
2-[2-methyl-4-((2R,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[3-fluoro-4-(2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-2-trifluoromethyl-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[2-methyl-4-((2R,3'S)-2-methyl-[1,3']bipyrrolidinyl-1'-yl)-phenyl]-9-oxa-2-aza-spiro[5.5]undecan-1-one;
2-[2-methyl-4-((2R,3'R)-2-methyl-[1,3']bipyrrolidinyl-1'-yl)-phenyl]-8-oxa-2-aza-spiro[4.5]decan-1-one;
2-[2-methyl-4-((2S,3'R)-2-methyl-[1,3']bipyrrolidinyl-1'-yl)-phenyl]-8-oxa-2-aza-spiro[4.5]decan-1-one;
2-[2-methyl-4-((2R,3'R)-2-methyl-[1,3']bipyrrolidinyl-1'-yl)-phenyl]-9-oxa-2-aza-spiro[5.5]undecan-1-one;
2-[2-methyl-4-((2S,3'R)-2-methyl-[1,3']bipyrrolidinyl-1'-yl)-phenyl]-9-oxa-2-aza-spiro[5.5]undecan-1-one;
2-[4-((2R,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'S)-2-Methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one; or
a salt thereof or an enantiomer or a diastereomer thereof.

7. The compound of claim 1 selected from the group consisting of:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-ethyl-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one;
2-[4-((2R,3'R)-2-methyl-[1,3']bipyrrolidinyl-1'-yl)-phenyl]-9-oxa-2-aza-spiro[5.5]undecan-1-one;
2-[4-((2S,3'R)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-9-oxa-2-aza-spiro[5.5]undecan-1-one;
2-[2-fluoro-4-((2R,3'R)-2-Methyl-[1,3']bipyrrolidinyl-1'-yl)-phenyl]-9-oxa-2-aza-spiro[5.5]undecan-1-one; and
2-[2-fluoro-4-((2S,3'R)-2-Methyl-[1,3']bipyrrolidinyl-1'-yl)-phenyl]-9-oxa-2-aza-spiro[5.5]undecan-1-one; or
a salt thereof or an enantiomer or a diastereomer thereof.

8. The compound of claim 1 selected from the group consisting of:
2-[2-methyl-4-((2S,3'S)-2-methyl-[1,3']bipyrrolidinyl-1'-yl)-phenyl]-8-oxa-2-aza-spiro[4.5]decan-1-one;
2-[2-methyl-4-((2S,3'S)-2-methyl-[1,3']bipyrrolidinyl-1'-yl)-phenyl]-9-oxa-2-aza-spiro[5.5]undecan-1-one;
2-[4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-8-oxa-2-aza-spiro[4.5]decan-1-one;
2-[2-fluoro-4-((2S,3'S)-2-methyl-[1,3']bipyrrolidinyl-1'-yl)-phenyl]-9-oxa-2-aza-spiro[5.5]undecan-1-one; and
2-[4-((2S,3'S)-2-methyl-[1,3']bipyrrolidinyl-1'-yl)-phenyl]-9-oxa-2-aza-spiro[5.5]undecan-1-one; or
a salt thereof or an enantiomer or a diastereomer thereof.

9. The compound according or claim 1 which has the formula (II):

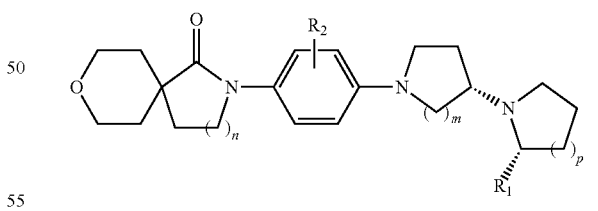

wherein $R_1$, $R_2$, m, n and p are as defined in claim 1.

10. A pharmaceutical composition comprising one or more compound of claim 1 or a pharmaceutically acceptable salt, an enantiomer, or a diastereomer thereof in combination with one or more pharmaceutically acceptable carriers, diluents or excipients.

11. A pharmaceutical composition comprising one or more compound of claim 2 or a pharmaceutically acceptable salt, an enantiomer, or a diastereomer thereof in combination with one or more pharmaceutically acceptable carriers, diluents or excipients.

12. A pharmaceutical composition comprising one or more compound of claim 3 or a pharmaceutically acceptable salt, an enantiomer, or a diastereomer thereof in combination with one or more pharmaceutically acceptable carriers, diluents or excipients.

13. A pharmaceutical composition comprising one or more compound of claim 4 or a pharmaceutically acceptable salt, an enantiomer, or a diastereomer thereof in combination with one or more pharmaceutically acceptable carriers, diluents or excipients.

14. A pharmaceutical composition comprising one or more compound of claim 5 or a pharmaceutically acceptable salt, an enantiomer, or a diastereomer thereof in combination with one or more pharmaceutically acceptable carriers, diluents or excipients.

15. A pharmaceutical composition comprising one or more compound of claim 6 or a pharmaceutically acceptable salt, an enantiomer, or a diastereomer thereof in combination with one or more pharmaceutically acceptable carriers, diluents or excipients.

16. A pharmaceutical composition comprising one or more compound of claim 7 or a pharmaceutically acceptable salt, an enantiomer, or a diastereomer thereof in combination with one or more pharmaceutically acceptable carriers, diluents or excipients.

17. A pharmaceutical composition comprising one or more compound of claim 8 or a pharmaceutically acceptable salt, an enantiomer, or a diastereomer thereof in combination with one or more pharmaceutically acceptable carriers, diluents or excipients.

18. A pharmaceutical composition comprising one or more compound of claim 9 or a pharmaceutically acceptable salt, an enantiomer, or a diastereomer thereof in combination with one or more pharmaceutically acceptable carriers, diluents or excipients.

19. A method for treating a disease in a patient, said disease selected from the group consisting of cognitive impairment associated with schizophrenia (CIAS), an anxiety disorder, major depressive disorder, dementia of Alzheimer type (DAT), cognitive deficits related to neurological diseases chosen from Alzheimer, Parkinson and Huntington, age related cognitive impairment, mild cognitive impairment, vascular dementia, Lewis Body dementia, cognition associated with cognitive deficits, a sleep disorder, attention deficit hyperactivity disorder and depression, and obesity, comprising administering to said patient a therapeutically effective amount of a compound according to claim 1.

20. The method according to claim 19, wherein the sleep disorder is selected from the group consisting of narcolepsy, circadian rhythm sleep disorder, obstructive sleep apnea, periodic limb movement and restless leg syndrome, excessive sleepiness and drowsiness due to medication side-effect.

21. The method according to claim 19, wherein the sleep disorder is narcolepsy.

22. The method according to claim 19, wherein the disease is cognitive impairment associated with schizophrenia (CIAS).

23. The method according to claim 19, wherein the disease is dementia of Alzheimer type (DAT).

24. The compound of claim 1 which is 2-[2-methyl-4-((2S,3'S)-2-methyl-[1,3']bipyrrolidinyl-1'-yl)-phenyl]-8-oxa-2-aza-spiro[4.5]decan-1-one;or a salt thereof or an enantiomer or a diastereomer thereof.

25. The compound of claim 1 which is 2-[2-methyl-4-((2S,3'S)-2-methyl-[1,3']bipyrrolidinyl-1'-yl)-phenyl]-9-oxa-2-aza-spiro[5.5]decan-1-one; or a salt thereof or an enantiomer or a diastereomer thereof.

26. The compound of claim 1 which is 2-[4-methyl-4-((2S,3'S)-2-methyl-[1,3']bipyrrolidinyl-1'-yl)-phenyl]-8-oxa-2-aza-spiro[4.5]decan-1-one; or a salt thereof or an enantiomer or a diastereomer thereof.

27. 2-[2-fluoro-4-((2S,3'S)-2-methyl-[1,3']bipyrrolidinyl-1'-yl)-phenyl]-8-oxa-2-aza-spiro[4.5]decan-1-one; or a salt thereof or an enantiomer or a diastereomer thereof.

28. A pharmaceutical composition comprising the compound of claim 24 or a pharmaceutically acceptable salt, an enantiomer, or a diastereomer thereof in combination with one or more pharmaceutically acceptable carriers, diluents or excipients.

29. A pharmaceutical composition comprising the compound of claim 25 or a pharmaceutically acceptable salt, an enantiomer, or a diastereomer thereof in combination with one or more pharmaceutically acceptable carriers, diluents or excipients.

30. A pharmaceutical composition comprising the compound of claim 26 or a pharmaceutically acceptable salt, an enantiomer, or a diastereomer thereof in combination with one or more pharmaceutically acceptable carriers, diluents or excipients.

31. A pharmaceutical composition comprising the compound of claim 27 or a pharmaceutically acceptable salt, an enantiomer, or a diastereomer thereof in combination with one or more pharmaceutically acceptable carriers, diluents or excipients.

* * * * *

UNITED STATES PATENT AND TRADEMARK OFFICE
CERTIFICATE OF CORRECTION

| | |
|---|---|
| PATENT NO. | : 8,217,052 B2 |
| APPLICATION NO. | : 13/151925 |
| DATED | : July 10, 2012 |
| INVENTOR(S) | : Zhongli Gao et al. |

It is certified that error appears in the above-identified patent and that said Letters Patent is hereby corrected as shown below:

On the Title page, in field (56), in column 2, under "Other Publications", line 2, delete "Ivan" and insert -- Van --, therefor.

In column 5, line 30, delete "[4,5]" and insert -- [4.5] --, therefor.

In column 5, line 52, delete "[4,5]" and insert -- [4.5] --, therefor.

In column 6, line 5, delete "pipendin" and insert -- piperidin --, therefor.

In column 6, line 7-8, delete "pipendin" and insert -- piperidin --, therefor.

In column 14, line 33-39, in Structure (20), delete " 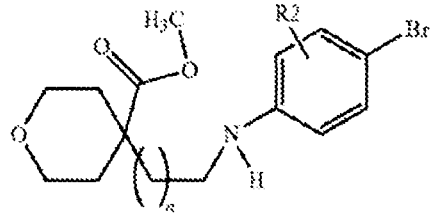 " and insert -- 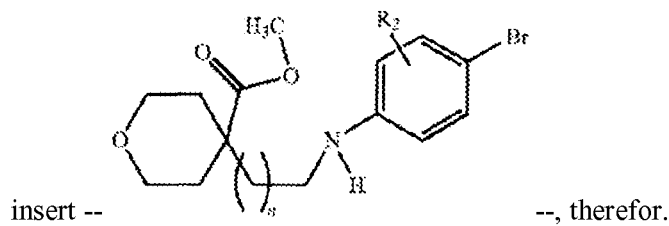 --, therefor.

Signed and Sealed this
Twenty-seventh Day of November, 2012

David J. Kappos
*Director of the United States Patent and Trademark Office*

CERTIFICATE OF CORRECTION (continued)
U.S. Pat. No. 8,217,052 B2

In column 14, line 42-50, in Structure (21), delete " 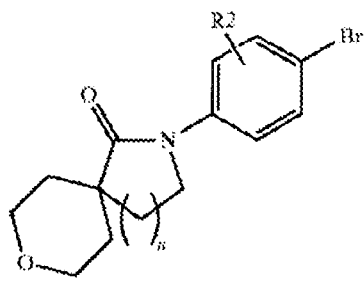 " and insert -- 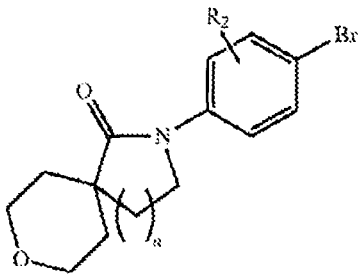 --, therefor.

In column 14, line 52-63, in Structure (18), delete " 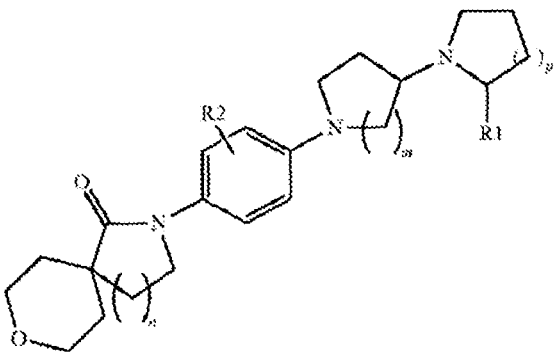 "

and insert -- 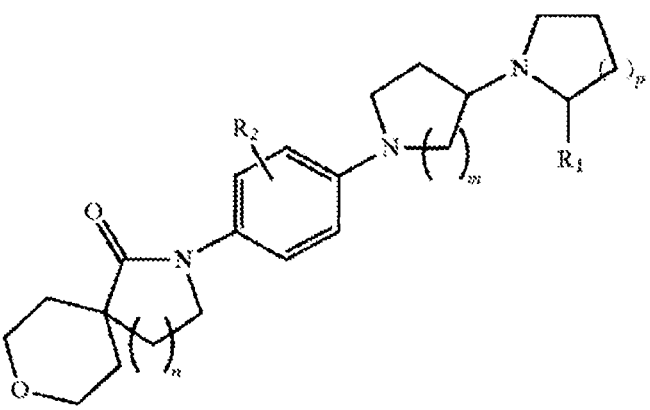 --, therefor.

In column 15, line 2, in Structure (21), delete " 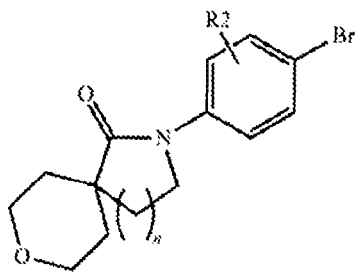 " and
insert -- 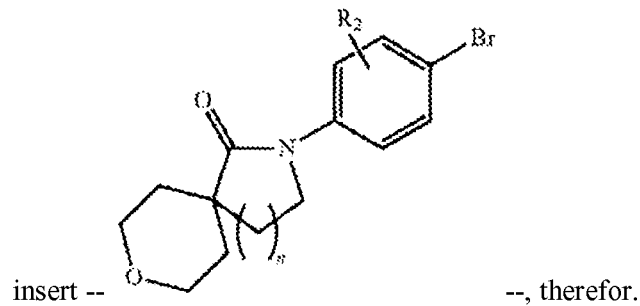 --, therefor.
In column 15-16, line 4, in Structure (21), delete
" 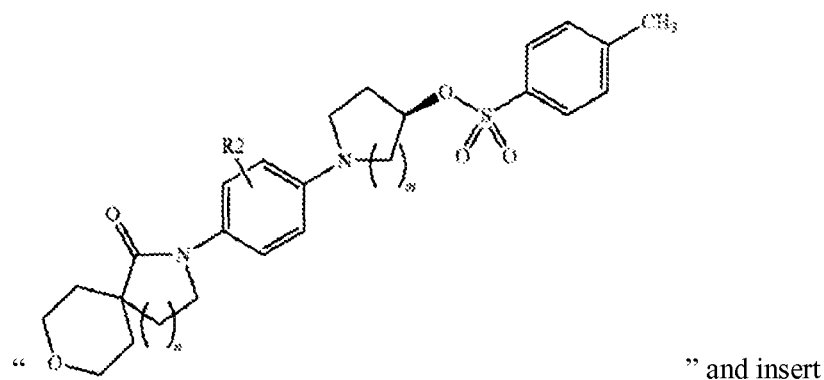 " and insert
-- 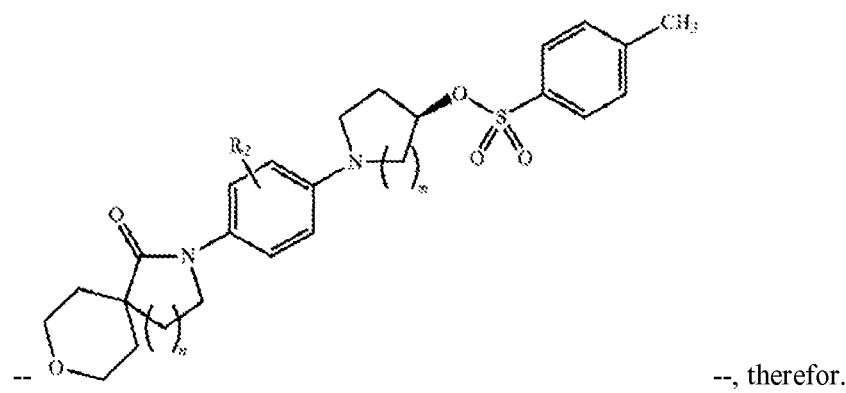 --, therefor.

In column 15, line 8, in Structure (18), below " 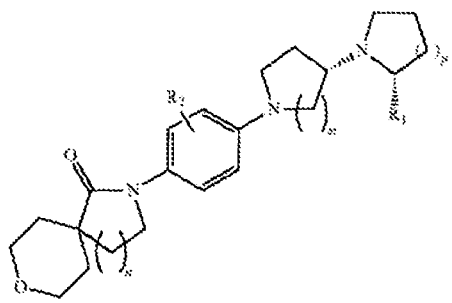 " delete "n, m, p = 1, 2".

In column 19, line 40, delete ""MeI"" and insert -- "MeI" --, therefor.

In column 19, line 46, delete ""M"" and insert -- "μM" --, therefor.

In column 20, line 26, delete "(AcN-F0.08%" and insert -- (AcN+0.08% --, therefor.

In column 20, line 27, delete "0.1')/0" and insert -- 0.1% --, therefor.

In column 21, line 11, delete "•HCl" and insert -- •2HCl --, therefor.

In column 21, line 55, delete "yl)piperidine" and insert -- yl)-piperidine --, therefor.

In column 23, line 29, delete "yl)piperidine" and insert -- yl)-piperidine --, therefor.

In column 25, line 3, delete "(M+H+)." and insert -- (M+H$^+$). --, therefor.

In column 30, line 25, delete "yl)piperidine" and insert -- yl)-piperidine --, therefor.

In column 30, line 42, delete "yl)piperidine" and insert -- yl)-piperidine --, therefor.

In column 35, line 3, delete "ethyl)tetrahydro" and insert -- ethyl)-tetrahydro --, therefor.

In column 35, line 19, delete "Na1O$_4$" and insert -- NaIO$_4$ --, therefor.

In column 40, line 25, delete "NaIO4" and insert -- NaIO4 --, therefor.

In column 41, line 46, delete "(iii)" and insert -- (Dii) --, therefor.

In column 42, line 1, delete "(viii)" and insert -- (Diii) --, therefor.

In column 44, line 17, delete "20-40:" and insert -- 20-40%: --, therefor.

In column 44, line 23, after "(q,"
insert -- 8.4Hz, 1H), 2.19-1.87 (m, 10H), 1.85-1.41 (m, 5H), 1.14 (d, 6.3Hz, 3H). --.

CERTIFICATE OF CORRECTION (continued)
U.S. Pat. No. 8,217,052 B2

In column 44, line 45, delete "40-50" and insert -- 40-50%, --, therefor.

In column 44, line 45, delete "50-70" and insert -- 50-70%, --, therefor.

In column 49, line 53-54, delete "yl)piperidine" and insert -- yl)-piperidine --, therefor.

In column 55, line 67, after "product" insert -- as --.

In column 57, line 35, delete "propyl)tetrahydro" and insert -- propyl)-tetrahydro --, therefor.

In column 57, line 45, delete "CH-2Cl2" and insert -- CH2Cl2 --, therefor.

In column 61, line 46, delete "(m, 2H," and insert -- (m, 2H), --, therefor.

In column 68, line 62, in claim 5, delete "((2R,3+S)" and insert -- ((2R,3'S) --, therefor.

In column 70, line 43, in claim 9, delete "or" and insert -- to --, therefor.

In column 72, line 15, in claim 24, delete "one;or" and insert -- one, or --, therefor.

In column 72, lines 21-22, in claim 26, delete "2-[4-methyl-4-((2S,3'S)-2-methyl" and insert -- 2-[4-((2S,3'S)-2-methyl --, therefor.